(12) United States Patent
Nomoto et al.

(10) Patent No.: US 9,156,889 B2
(45) Date of Patent: Oct. 13, 2015

(54) DRUG TRANSPORTER PERMEATING BLOOD-BRAIN BARRIER, PEPTIDE AND USE THEREOF

(71) Applicants: Microbial Chemistry Research Foundation, Tokyo (JP); ImmunoFuture, Inc., Tokyo (JP)

(72) Inventors: Akio Nomoto, Tokyo (JP); Coh-ichi Nihei, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 13/955,319

(22) Filed: Jul. 31, 2013

(65) Prior Publication Data

US 2013/0337050 A1 Dec. 19, 2013

Related U.S. Application Data

(63) Continuation of application No. PCT/JP2012/052225, filed on Feb. 1, 2012.

(30) Foreign Application Priority Data

Feb. 2, 2011 (JP) ................. 2011-021224

(51) Int. Cl.
| | |
|---|---|
| C07K 7/06 | (2006.01) |
| C07K 7/08 | (2006.01) |
| C07K 14/005 | (2006.01) |
| A61K 47/42 | (2006.01) |
| A61K 39/13 | (2006.01) |
| C07K 14/00 | (2006.01) |
| A61K 38/00 | (2006.01) |

(52) U.S. Cl.
CPC ............. *C07K 14/005* (2013.01); *A61K 39/13* (2013.01); *A61K 47/42* (2013.01); *C07K 7/06* (2013.01); *C07K 7/08* (2013.01); *C07K 14/001* (2013.01); *A61K 38/00* (2013.01)

(58) Field of Classification Search
CPC .......... C07K 7/06; C07K 7/08; C07K 14/105; C07K 14/08; C07K 17/082; C07K 14/085
See application file for complete search history.

(56) References Cited

U.S. PATENT DOCUMENTS

| 6,635,248 B1 | 10/2003 | Ternynck et al. | |
|---|---|---|---|
| 7,476,499 B2* | 1/2009 | Kirkegaard et al. | ............... 435/5 |
| 2007/0166401 A1 | 7/2007 | Park | |
| 2009/0104218 A1* | 4/2009 | Tettelin et al. | ............. 424/190.1 |

FOREIGN PATENT DOCUMENTS

| EP | 0180490 | 7/1986 |
|---|---|---|
| JP | 2004-292399 | 10/2004 |
| JP | 2009-159988 | 7/2009 |
| JP | 2009-298800 | 12/2009 |
| WO | 2004/060403 | 7/2004 |

OTHER PUBLICATIONS

Hwang et al., "Use of Fluorescence Resonance Energy Transfer for Rapid Detection of Enteroviral Infection In Vivo", Applied and Environmental Microbiology, 2006, pp. 3710-3715.*
McKinlay et al., "Prevention of human poliovirus-induced paralysis and death in mice by the antiviral agent arildone", Antimicrob. Agents Chemother, 1982, pp. 1022-1025.*
National Institute of Neurological Disorders and Stroke, "Post-Polio Syndrom Fact Sheet", Apr. 2014, pp. 1-6.*
Chow et al., "Synthetic peptides from four separate regions of the poliovirus type 1 capsid protein VP1 induce neutralizing antibodies", PNAS, 1985, p. 910-914.*
Leclerc et al., "Identification of a T-Cell Epitope Adjacent to Neutralization Antigenic Site 1 of Poliovirus Type 1", Journal of Virology, 1991, pp. 711-718.*
Belnap et al., "Three-dimensional structure of poliovirus receptor bound to poliovirus", PNAS, 2000, pp. 73-78.*
Ohka et al., "Poliovirus trafficking toward central nervous system via human poliovirus receptor-dependent and -independent pathway", Front. Microbiol., Apr. 18, 2012, pp. 1-4.*
Chain 1, Crystal Structure of Mahoney Strain of Poliovirus at 2.2a Resolution, Accession No. 1HXS_1; deposited Jan. 16, 2011; obtained from http://www.ncbi.nlm.nih.gov/protein/1HXS_1 on Mar. 2, 2015.*
Yang, W.X. et al., "Efficient Delivery of Circulating Poliovirus to the Central Nervous System Independently of Poliovirus Receptor," Virology, Mar. 17, 1997, 229(2), pp. 421-428.

(Continued)

*Primary Examiner* — Karlheinz R Skowronek
*Assistant Examiner* — Lianko Garyu
(74) *Attorney, Agent, or Firm* — Carmody Torrance Sandak & Hennessey LLP

(57) ABSTRACT

A peptide, wherein the peptide comprises an amino acid sequence expressed by the following SEQ ID NO: 1, an amino acid sequence expressed by the following SEQ ID NO: 2, an amino acid sequence expressed by the following SEQ ID NO: 3, an amino acid sequence expressed by the following SEQ ID NO: 4, or any combination thereof:

Figure 1:
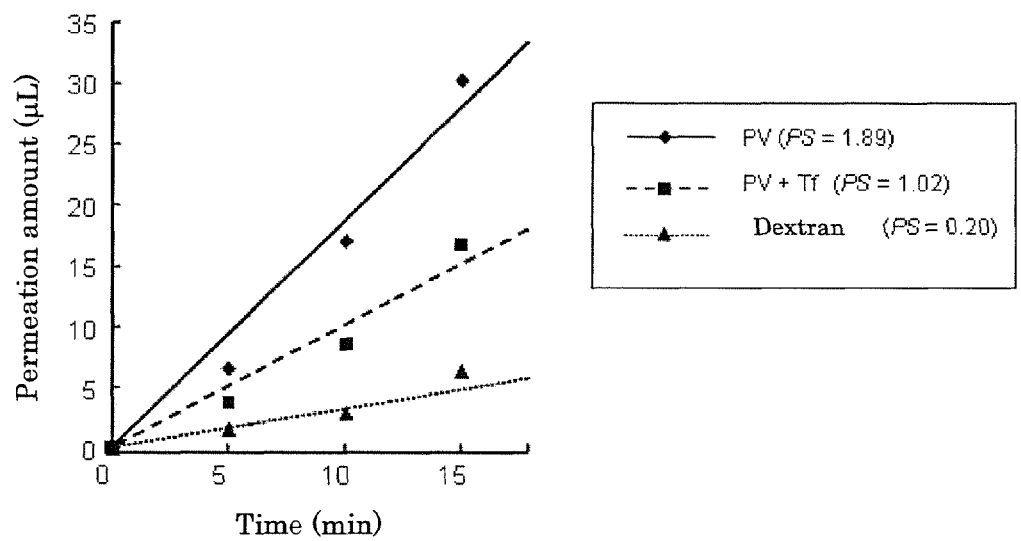
Figure 2:
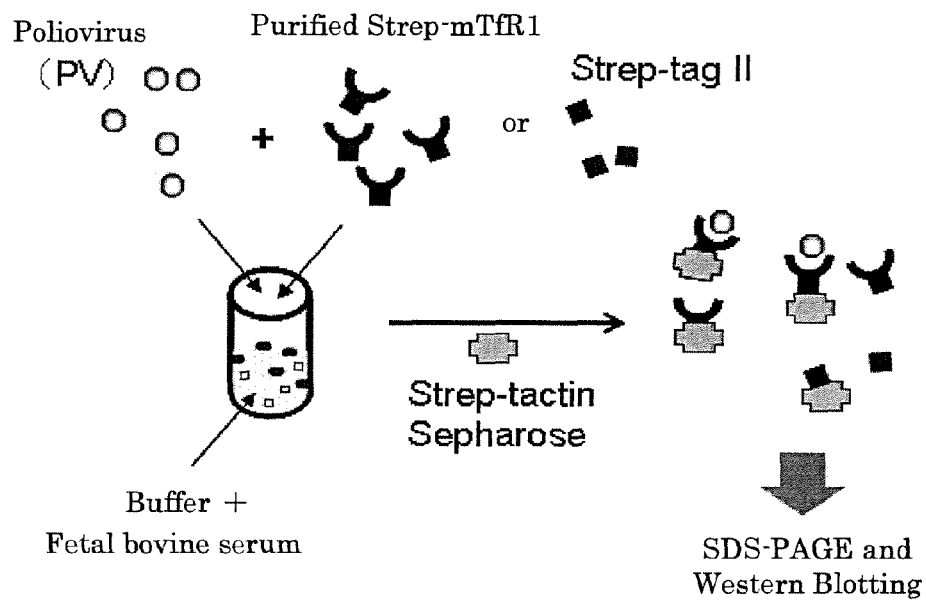
Figure 3:
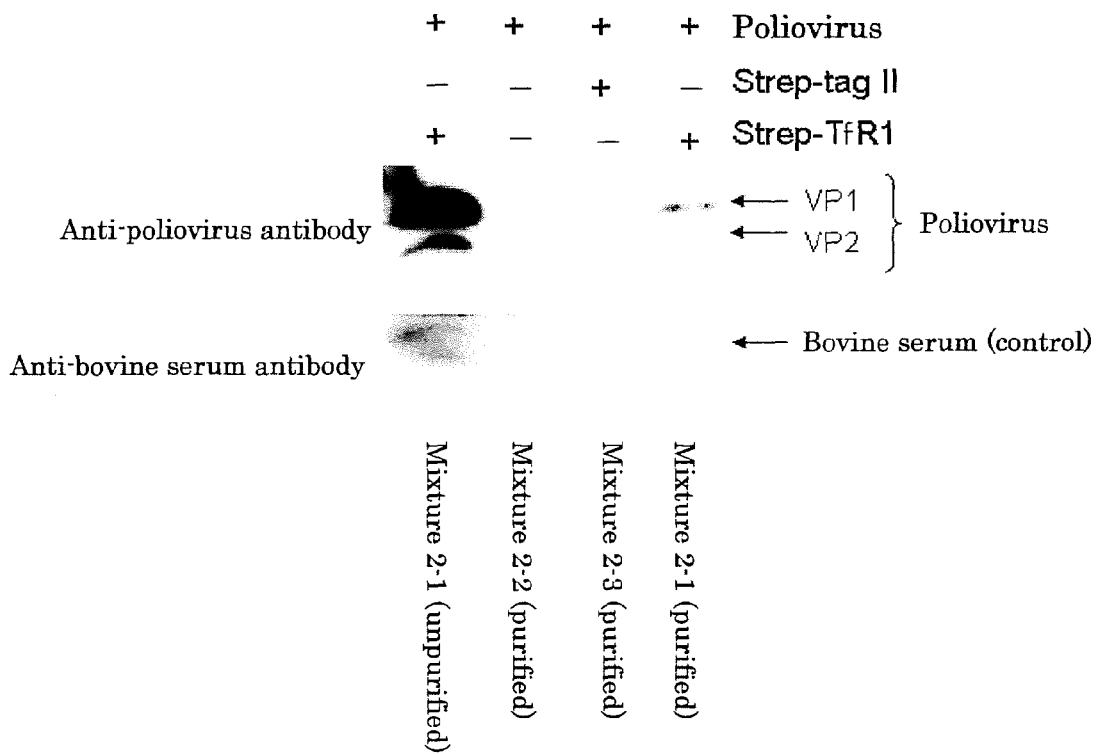

```
                                          (SEQ ID NO: 1)
ALGDSLYGAASLN;

(SEQ ID NO: 2)
MTVDNPASTTNKDKLFSVWK;

(SEQ ID NO; 3)
PGAVPEK;
and (SEQ ID NO: 4)
STKDLTTY.
```

18 Claims, 8 Drawing Sheets

(56) References Cited

OTHER PUBLICATIONS

Koike, S. et al., "The Poliovirus Receptor Protein is Produced both as Membrane-Bound and Secreted Forms," The EMBO Journal, Oct. 1990, vol. 9, No. 10, pp. 3217-3224.

Coh-ichi Nihel, Akio Nomoto, "Permeation Mechanism of Poliovirus Through Blood-Brain Barrier," Program and Proceedings of the 58th Annual Meeting of the Japanese Society for Virology, Oct. 15, 2010, p. 325, P1-001.

Coh-ichi Nihel, Akio Nomoto, "Characterization of Virus-Binding Site on Transferrin Receptor," 32nd Annual Meeting of the Molecular Biology Society of Japan PDF Proceedings, Dec. 16, 2009, p. 244, 1p-0801.

Seii Ohka, "4. Dissemination Pathways for Poliovirus: Cells to Animal Models," Virus, 2006, vol. 56, No. 1, pp. 51-58.

Coyne, C.B., Poliovirus Entry into Human Brain Microvascular Cells Requires Receptor-Induced Activation of SHP-2, The EMBO Journal, 2007, vol. 26, No. 17, p. 4016-4028.

Mueller et al., Poliovirus and poliomyelitis: A tale of guts, brains and an accidental event, Virus Research, vol. 111, No. 2, Aug. 2005, pp. 175-193.

Ohka et al., Recent insights into poliovirus pathogenesis, Trends in Microbiolongy, vol. 9, No. 10, Oct. 2001, pp. 501-506.

Belnap et al., Molecular Tectonic Model of Virus Structural Transitions: the Putative Cell Entry States of Poliovirus, Journal of Virology, vol. 74, No. 3, Feb. 2000, pp. 1342-1354.

He et al., Interaction of the poliovirus receptor with poliovirus, Proceedings of the National Academy of Sciences, vol. 97, No. 1, Jan. 2000, pp. 79-84.

Kitamura et al., Primary structure, gene organization and polypeptide expression of poliovirus RNA, Nature, vol. 291, Jun. 1981, pp. 547-553.

* cited by examiner

FIG. 8

FIG. 9

| | | | | | | |
|---|---|---|---|---|---|---|
| + | + | + | + | + | + | GST-mTfR1 |
| − | − | + | − | − | − | MBP |
| − | − | − | + | − | − | MBP-VP1GH Strand I |
| − | − | − | − | + | − | MBP-VP1GH Strand II |
| + | − | − | − | − | + | MBP-VP1GH Loop |

Anti-mTfR1 antibody  ▬    ▬ ▬ ▬ ← GST-mTfR1 (PV binding region)

Mixture 5-1 (unpurified)
Mixture 5-2 (purified)
Mixture 5-3 (purified)
Mixture 5-4 (purified)
Mixture 5-5 (purified)
Mixture 5-1 (purified)

FIG. 10

```
+  +  +  +  +  +  +   GST-mTfR1
-  +  -  -  -  -  -   MBP
-  -  +  -  -  -  -   MBP-VP1BC Loop
-  -  -  +  -  -  -   MBP-VP1EF Loop
+  -  -  -  +  -  -   MBP-VP1FG Loop
-  -  -  -  -  +  -   MBP-VP1GH Loop
-  -  -  -  -  -  +   MBP-VP1C Terminus
```

Anti-mTfR1 antibody ← GST-mTfR1 (PV binding region)

Mixture 6-1 (unpurified), Mixture 6-2 (purified), Mixture 6-3 (purified), Mixture 6-4 (purified), Mixture 6-1 (purified), Mixture 6-5 (purified), Mixture 6-6 (purified)

FIG. 11

- ▲ Alexa488-MBP-VP1GH Loop
- ■ Alexa488-mTf
- ● Dextran (cont.)
- ♦ Alexa488-MBP (cont.)

X-axis: Time (min), Y-axis: Permeation amount (μL)

SEQUENCE LISTING

```
<160> NUMBER OF SEQ ID NOS: 25

<210> SEQ ID NO 1
<211> LENGTH: 13
<212> TYPE: PRT
<213> ORGANISM: poliovirus

<400> SEQUENCE: 1

Ala Leu Gly Asp Ser Leu Tyr Gly Ala Ala Ser Leu Asn
1               5                   10

<210> SEQ ID NO 2
<211> LENGTH: 20
<212> TYPE: PRT
<213> ORGANISM: poliovirus

<400> SEQUENCE: 2

Met Thr Val Asp Asn Pro Ala Ser Thr Thr Asn Lys Asp Lys Leu Phe
1               5                   10                  15

Ser Val Trp Lys
            20

<210> SEQ ID NO 3
<211> LENGTH: 7
<212> TYPE: PRT
<213> ORGANISM: poliovirus

<400> SEQUENCE: 3

Pro Gly Ala Val Pro Glu Lys
1               5

<210> SEQ ID NO 4
<211> LENGTH: 8
<212> TYPE: PRT
<213> ORGANISM: poliovirus

<400> SEQUENCE: 4

Ser Thr Lys Asp Leu Thr Thr Tyr
1               5

<210> SEQ ID NO 5
<211> LENGTH: 9
<212> TYPE: PRT
```

```
<213> ORGANISM: Mus musculus

<400> SEQUENCE: 5

Thr Gln Phe Pro Pro Ser Gln Ser Ser
1               5

<210> SEQ ID NO 6
<211> LENGTH: 9
<212> TYPE: PRT
<213> ORGANISM: Homo sapiens

<400> SEQUENCE: 6

Thr Gln Phe Pro Pro Ser Arg Ser Ser
1               5

<210> SEQ ID NO 7
<211> LENGTH: 9
<212> TYPE: PRT
<213> ORGANISM: Homo sapiens

<400> SEQUENCE: 7

Thr Gln Phe Pro Pro Val Ala Ser Ser
1               5

<210> SEQ ID NO 8
<211> LENGTH: 9
<212> TYPE: PRT
<213> ORGANISM: Mus musculus

<400> SEQUENCE: 8

Thr Gln Phe Pro Pro Val Glu Ser Ser
1               5

<210> SEQ ID NO 9
<211> LENGTH: 53
<212> TYPE: DNA
<213> ORGANISM: artifical sequence
<220> FEATURE:
<223> OTHER INFORMATION: primer

<400> SEQUENCE: 9
gctctagaga ccaatcagca gcgttgggcg attcacttta tggtgctgca tcc          53

<210> SEQ ID NO 10
<211> LENGTH: 48
<212> TYPE: DNA
<213> ORGANISM: artifical sequence
<220> FEATURE:
<223> OTHER INFORMATION: primer

<400> SEQUENCE: 10
cccaagcttc tattattagt tcaaggatgc agcaccataa agtgaatc                48

<210> SEQ ID NO 11
<211> LENGTH: 59
<212> TYPE: DNA
<213> ORGANISM: artifical sequence
<220> FEATURE:
<223> OTHER INFORMATION: primer

<400> SEQUENCE: 11
gctctagaat gactgtggac aacccggctt ctactacaaa caaagacaaa ttgttttct    59

<210> SEQ ID NO 12
<211> LENGTH: 54
```

```
<212> TYPE: DNA
<213> ORGANISM: artifical sequence
<220> FEATURE:
<223> OTHER INFORMATION: primer

<400> SEQUENCE: 12
cccaagcttc tattattact tccacacaga aaacaatttg tctttgtttg tagt         54

<210> SEQ ID NO 13
<211> LENGTH: 36
<212> TYPE: DNA
<213> ORGANISM: artifical sequence
<220> FEATURE:
<223> OTHER INFORMATION: primer

<400> SEQUENCE: 13
gctctagacc aggggcaccg gtgccagaga aataat                              36

<210> SEQ ID NO 14
<211> LENGTH: 36
<212> TYPE: DNA
<213> ORGANISM: artifical sequence
<220> FEATURE:
<223> OTHER INFORMATION: primer

<400> SEQUENCE: 14
cccaagcttc tattattatt tctctggcac cggtgc                              36

<210> SEQ ID NO 15
<211> LENGTH: 49
<212> TYPE: DNA
<213> ORGANISM: artifical sequence
<220> FEATURE:
<223> OTHER INFORMATION: primer

<400> SEQUENCE: 15
gctctagact cgctccctta tccaccaaag acctgacaac gtacgctag                49

<210> SEQ ID NO 16
<211> LENGTH: 43
<212> TYPE: DNA
<213> ORGANISM: artifical sequence
<220> FEATURE:
<223> OTHER INFORMATION: primer

<400> SEQUENCE: 16
cccaagcttc tattattagt acgttgtcag gtctttggtg gat                      43

<210> SEQ ID NO 17
<211> LENGTH: 34
<212> TYPE: DNA
<213> ORGANISM: artifical sequence
<220> FEATURE:
<223> OTHER INFORMATION: primer

<400> SEQUENCE: 17
tccccgcggt cgcttatatt gggcagacct caaa                                34

<210> SEQ ID NO 18
<211> LENGTH: 31
<212> TYPE: DNA
<213> ORGANISM: artifical sequence
<220> FEATURE:
<223> OTHER INFORMATION: primer

<400> SEQUENCE: 18
```

```
ccgctcgagt ccaaccccgc actaaaagct g                                     31
```

<210> SEQ ID NO 19
<211> LENGTH: 33
<212> TYPE: PRT
<213> ORGANISM: poliovirus

<400> SEQUENCE: 19

Ser Lys Val Pro Leu Lys Asp Gln Ser Ala Glu Leu Gly Asp Ser Leu
1               5                   10                  15

Tyr Gly Ala Ala Ser Leu Asn Asp Phe Gly Ile Leu Ala Val Arg Val
            20                  25                  30

Val

<210> SEQ ID NO 20
<211> LENGTH: 33
<212> TYPE: PRT
<213> ORGANISM: poliovirus

<400> SEQUENCE: 20

Ser Lys Val Pro Leu Lys Asp Gln Ser Ala Ala Leu Gly Asp Ser Leu
1               5                   10                  15

Tyr Gly Ala Ala Ser Leu Asn Asp Phe Gly Ile Leu Ala Val Arg Val
20 25 30

Val

<210> SEQ ID NO 21
<211> LENGTH: 65
<212> TYPE: DNA
<213> ORGANISM: artifical sequence
<220> FEATURE:
<223> OTHER INFORMATION: primer

<400> SEQUENCE: 21
gctctagaca aacgtcctcc aacccatcaa ttttctacac ctacggcacg gcaccagctc 60
gaatt 65

<210> SEQ ID NO 22
<211> LENGTH: 78
<212> TYPE: DNA
<213> ORGANISM: artifical sequence
<220> FEATURE:
<223> OTHER INFORMATION: primer

<400> SEQUENCE: 22
cccaagcttt tactattaat acgcgttaga aatgccaacg tatggaaccg aaattcgagc 60
tggtgccgtg ccgtaggt 78

<210> SEQ ID NO 23
<211> LENGTH: 25
<212> TYPE: PRT
<213> ORGANISM: poliovirus

<400> SEQUENCE: 23

Pro Ser Ile Phe Tyr Thr Tyr Gly Thr Ala Pro Ala Arg Ile Ser Val
1 5 10 15

Pro Tyr Val Gly Ile Ser Asn Ala Tyr
20 25

<210> SEQ ID NO 24
<211> LENGTH: 36

```
<212> TYPE: DNA
<213> ORGANISM: artifical sequence
<220> FEATURE:
<223> OTHER INFORMATION: primer

<400> SEQUENCE: 24
ccgctcgagg ccaccatgat ggatcaagcc agatca                               36

<210> SEQ ID NO 25
<211> LENGTH: 31
<212> TYPE: DNA
<213> ORGANISM: artifical sequence
<220> FEATURE:
<223> OTHER INFORMATION: primer

<400> SEQUENCE: 25
cgcggatccc gaaactcatt gtcaatattc c                                    31
```

DRUG TRANSPORTER PERMEATING BLOOD-BRAIN BARRIER, PEPTIDE AND USE THEREOF

CROSS-REFERENCE TO RELATED APPLICATION

This is a continuation application of PCT/JP2012/052225, filed on Feb. 1, 2012.

This application incorporates by reference the material contained in the ASCII text file submitted herewith. The text file contains the file entitled Sequence Listing N-BK003-11P_ST25.txt, which was created on Dec. 19, 2011.

BACKGROUND OF THE INVENTION

1. Field of the Invention

The present invention relates to a peptide that permeates the blood-brain barrier, a drug transporter, an antipoliovirus agent, a blood-brain barrier permeating agent, and a transferrin receptor capturing body.

2. Description of the Related Art

The blood-brain barrier (BBB) in the central nervous system strictly restricts intake of substances to the central nervous system. This is because the blood-brain barrier is physically narrowed with densely populated vascular endothelial cells and other cells, and these cells have physiological functions of restricting intake of substances. The mechanism of permeation of substances through the blood-brain barrier has not yet been revealed. At present, even if disorders occur in the central nervous system, drugs cannot be delivered to target sites in the central nervous system.

Disorders in the central nervous system include: infections caused by, for example, poliovirus and Japanese encephalitis virus; and neurodegenerative diseases such as Alzheimer's disease, Parkinson's disease and Huntington's chorea. Infections in the central nervous system have been prevented by vaccination, and infected patients have mainly undergone symptomatic therapy. In this manner, effective therapeutic methods have not yet been found.

One proposed therapeutic drug against poliovirus is an antivirus agent composition containing citric acid and/or zinc, L-arginine and an acceptable carrier (see Japanese Patent Application Laid-Open (JP-A) No. 2009-298800) and another proposed therapeutic drug is an antivirus agent containing selegiline as an active ingredient (see JP-A No. 2004-292399). These antivirus agents cannot permeate the blood-brain barrier, which is problematic in use.

In an attempt to utilize drugs more safely and effectively, the recent interest has focused not only on the dosage form suitable to drugs but also on drug delivery methods for efficiently delivering drugs to target sites in the body. In particular, demand has arisen for practical use of a drug delivery system (DDS) as a transporting system for delivering a drug at a required timing in a required amount to a required site.

In the central nervous system, a method using a virus vector has been proposed (see, for example, JP-A No. 2009-159988). However, this method has a problem in terms of safety and has not been practically used so far. At present, there has not been found a DDS that allows drugs to permeate the blood-brain barrier.

Meanwhile, viruses permeate the blood-brain barrier to infect the central nervous system. For example, poliovirus (PV), which is a positive single-stranded RNA virus belonging to the genus Enterovirus of the family Picornaviridae, is a cause of polio (poliomyelitis) and known to have neurotropism. A natural host thereof is only human but experimentally, poliovirus can infect primates. Poliovirus infects human via an oral route, proliferates in the digestive tract, and invades blood via the tonsil or the Peyer's patch. Then, poliovirus permeates the blood-brain barrier to invade the central nervous system, where it mainly infects motor nerve cells to destroy their cell functions. As a result, infected patients suffer from paralysis of their limbs. The central nervous system is also known to have a route through which poliovirus is transported from the skeletal muscle in a retrograde fashion on the nerve axon to reach motor nerve cells.

As for a poliovirus receptor (PVR), CD155 is known to be involved with poliovirus infection (see Koike S et al., EMBO J. 1990 October; 9(10): 3217-24.).

However, studies using a transgenic mouse with a PVR gene introduced suggest that CD155 is not involved with the permeation of poliovirus through the blood-brain barrier (see Yang W X et al., Virology. 1997 Mar. 17; 229(2): 421-8.). This finding indicates that another receptor is presumably involved with the permeation of poliovirus through the blood-brain barrier.

Although revealing the mechanism of poliovirus infection is thought to reveal the blood-brain barrier permeation mechanism from blood to the central nervous system, the mechanism of poliovirus infection has not yet been revealed.

SUMMARY OF THE INVENTION

The present invention aims to solve the above problems pertinent in the art and achieve the following object. That is, an object of the present invention is to provide: a peptide capable of permeating the blood-brain barrier; a drug transporter capable of transporting a drug to a target cell in the central nervous system; an antipoliovirus agent capable of preventing development of a disease caused by poliovirus; a blood-brain barrier permeating agent; and a transferrin receptor capturing body.

The present inventors conducted extensive studies to solve the above problems and have found the following finding. That is, they found that a peptide including an amino acid sequence expressed by the following SEQ ID NO: 1, an amino acid sequence expressed by the following SEQ ID NO: 2, an amino acid sequence expressed by the following SEQ ID NO: 3, an amino acid sequence expressed by the following SEQ ID NO: 4, or any combination thereof permeates the blood-brain barrier, accomplishing the present invention on the basis of this finding.

The present invention is based on the above finding obtained by the present inventors, and means for solving the above problem are as follows.

<1> A peptide, wherein the peptide includes an amino acid sequence expressed by the following SEQ ID NO: 1, an amino acid sequence expressed by the following SEQ ID NO: 2, an amino acid sequence expressed by the following SEQ ID NO: 3, an amino acid sequence expressed by the following SEQ ID NO: 4, or any combination thereof:

```
                              (SEQ ID NO: 1)
ALGDSLYGAASLN;

(SEQ ID NO: 2)
MTVDNPASTTNKDKLFSVWK;

(SEQ ID NO: 3)
PGAVPEK;
and (SEQ ID NO: 4)
STKDLTTY.
```

<2> The peptide according to <1>, wherein the peptide permeates blood-brain barrier.

<3> The peptide according to <1> or <2>, wherein the peptide binds to a transferrin receptor.

<4> The peptide according to <3>, wherein the peptide binds to an AD (Apical domain) of the transferrin receptor.

<5> The peptide according to any one of <1> to <4>, wherein the peptide binds to an amino acid sequence expressed by the following SEQ ID NO: 5, an amino acid sequence expressed by the following SEQ ID NO: 6, an amino acid sequence expressed by the following SEQ ID NO: 7, an amino acid sequence expressed by the following SEQ ID NO: 8, or any combination thereof:

```
                              (SEQ ID NO: 5)
TQFPPSQSS;

(SEQ ID NO: 6)
TQFPPSRSS;

(SEQ ID NO: 7)
TQFPPVASS;
and (SEQ ID NO: 8)
TQFPPVESS.
```

<6> A drug transporter including:
the peptide according to any one of <1> to <5>.

<7> The drug transporter according to <6>, further including: a carrier.

<8> The drug transporter according to <7>, wherein the carrier is a macromolecule, a microassembly, a microparticle, a microsphere, a nanosphere, a liposome, an emulsion, or any combination thereof.

<9> The drug transporter according to <7> or <8>, further including: a drug carried in the carrier, wherein the drug is for diagnosis, prevention, treatment, or any combination thereof.

<10> The drug transporter according to <9>, wherein the drug for diagnosis, prevention, treatment, or any combination thereof is a nucleic acid, a polynucleotide, a gene, an analog thereof, glycosaminoglycan, a derivative thereof, oligosaccharide, polysaccharide, a derivative thereof, a protein, a peptide, an antineurotic agent, an antivirus agent, an anticancer agent, an antibiotics, an enzyme drug, an antioxidant, an anti-inflammatory agent, a steroid drug, an angiotensin converting enzyme inhibitor, a vasodilating agent, an inhibitor of proliferation and/or migration of smooth muscle cells, a platelet aggregation inhibitor, an anticoagulant, a chemical mediator release inhibitor, an immunosuppressant, a lipid intake inhibitor, a hormone drug, an angiotensin receptor antagonist, an agent for proliferating or suppressing vascular endothelial cells, an aldose reductase inhibitor, a mesangial cell proliferation inhibitor, a lipoxygenase inhibitor, an immunopotentiating agent, a Maillard reaction suppressor, an amyloidosis inhibitor, a nitric oxide synthase inhibitor, an advanced glycation endproducts inhibitor, a radical scavenger, or any combination thereof.

<11> The drug transporter according to any one of <6> to <10>, wherein the drug transporter is transported into a cell through endocytosis.

<12> The drug transporter according to <11>, wherein the cell is a vascular endothelial cell.

<13> The drug transporter according to any one of <6> to <12>, wherein the drug transporter is used for oral administration.

<14> An antipoliovirus agent, including:

the peptide according to any one of <1> to <5>, wherein the antipoliovirus agent prevents development of a disease caused by poliovirus.

<15> A blood-brain barrier permeating agent, including:

the peptide according to any one of <1> to <5>, wherein the blood-brain barrier permeating agent permeates blood-brain barrier.

<16> A transferrin receptor capturing body, including:

the peptide according to any one of <1> to <5>, wherein the transferrin receptor capturing body binds to a transferrin receptor.

The present invention can provide: a peptide capable of permeating the blood-brain barrier; a drug transporter capable of transporting a drug to a target cell in the central nervous system; an antipoliovirus agent capable of preventing development of a disease caused by poliovirus; a blood-brain barrier permeating agent; and a transferrin receptor capturing body, which can solve the above problems pertinent in the art and achieve the above object.

BRIEF DESCRIPTION OF THE DRAWINGS

FIG. 1 is a graph of results obtained in a blood-brain barrier permeation test of poliovirus in Test Example 1, where the vertical axis is permeation amount (μL) and the horizontal axis is time (min).

FIG. 2 is a schematic, explanatory representation of Test Example 2.

FIG. 3 illustrates results of western blotting in Test Example 2.

FIG. 4 is a schematic, explanatory view of a domain structure of a mouse transferrin receptor 1 (mTfR1).

FIG. 5 is a schematic, explanatory view of a construct produced in Test Example 3.

FIG. 6 is a schematic, explanatory representation for studies by western blotting in Test Examples 4-1 and 4-2.

FIG. 7-1 illustrates results of western blotting in Test Example 4-1.

FIG. 7-2 illustrates results of western blotting in Test Example 4-2.

FIG. 8 depicts a stearic configuration (2.2 angstroms) of poliovirus (Mahoney strain) determined by X-ray crystallographic analysis (PDB ID:1HXS).

FIG. 9 illustrates results of western blotting in Test Example 5.

FIG. 10 illustrates results of western blotting in Test Example 6.

FIG. 11 is a graph of results obtained in a blood-brain barrier permeation test of a peptide expressed by SEQ ID NO: 1 in Test Example 7, where the vertical axis is permeation amount (μL) and the horizontal axis is time (min).

FIG. 12A depicts a simulation model of a complex of VP1, VP2 and VP3 of poliovirus.

FIG. 12B depicts a simulation model enlarging VP1 of poliovirus.

FIG. 12C depicts a simulation model of a transferrin receptor.

FIG. 12D depicts a simulation model where a complex of VP1, VP2 and VP3 of poliovirus is bound to a transferrin receptor.

DETAILED DESCRIPTION OF THE INVENTION

Peptide

A peptide of the present invention includes an amino acid sequence expressed by the following SEQ ID NO: 1, an amino acid sequence expressed by the following SEQ ID NO:

2, an amino acid sequence expressed by the following SEQ ID NO: 3, an amino acid sequence expressed by the following SEQ ID NO: 4, or any combination thereof. The peptide mainly has a function of permeating the blood-brain barrier.

N terminus-ALGDSLYGAASLN-C terminus (SEQ ID NO: 1)

N terminus-MTVDNPASTTNKDKLFSVWK-C terminus (SEQ ID NO: 2)

N terminus-PGAVPEK-C terminus (SEQ ID NO: 3)

N terminus-STKDLTTY-C terminus (SEQ ID NO: 4)

So long as the peptide permeates the blood-brain barrier, the peptide may consist of an amino acid sequence that is identical to each of the amino acid sequences expressed by SEQ ID NOs: 1 to 4, or any combination thereof except that one or several amino acids are substituted, deleted or added in the entirety or a part thereof. Also, the N or C terminus of the peptide may be subjected to chemical modification. The chemical modification is not particularly limited and may be appropriately selected depending on the intended purpose. Examples thereof include acetylation, myristoylation, amidation and cystinylation.

The peptide may consist of each of the amino acid sequences expressed by SEQ ID NOs: 1 to 4, or any combination thereof.

The method for obtaining the peptide is not particularly limited and may be appropriately selected depending on the intended purpose. Examples thereof include: a method of chemically synthesizing the peptide; and a method of obtaining the peptide by a molecular biological technique based on a gene sequence of poliovirus (PV).

The method of chemically synthesizing the peptide is not particularly limited and may be appropriately selected depending on the intended purpose. Examples thereof include a method where the peptide is chemically synthesized using a peptide synthesizer (e.g., product of Shimadzu Corporation Ltd.).

The method of obtaining the peptide by a molecular biological technique based on a gene sequence of poliovirus is not particularly limited and may be appropriately selected depending on, for example, a sequence of the peptide. Examples thereof include a method where a genome RNA prepared from poliovirus is treated with a reverse transcriptase to synthesize cDNA, which is used as a template and amplified by a PCR method, followed by cloning.

The primers used for the PCR method are not particularly limited and may be appropriately selected depending on the intended purpose so long as they can amplify each of the amino acid sequences expressed by SEQ ID NOs: 1 to 4, or any combination thereof. In the case of amplifying the amino acid sequence expressed by SEQ ID NO: 1, it is preferable to use a sense primer expressed by the following SEQ ID NO: 9 and an antisense primer expressed by the following SEQ ID NO: 10. In the case of amplifying the amino acid sequence expressed by SEQ ID NO: 2, it is preferable to use a sense primer expressed by the following SEQ ID NO: 11 and an antisense primer expressed by the following SEQ ID NO: 12. In the case of amplifying the amino acid sequence expressed by SEQ ID NO: 3, it is preferable to use a sense primer expressed by the following SEQ ID NO: 13 and an antisense primer expressed by the following SEQ ID NO: 14. In the case of amplifying the amino acid sequence expressed by SEQ ID NO: 4, it is preferable to use a sense primer expressed by the following SEQ ID NO: 15 and an antisense primer expressed by the following SEQ ID NO: 16.

```
Sense primer:
                                                 (SEQ ID NO: 9)
5'-GCTCTAGAGACCAATCAGCAGCGTTGGGCGATTCACTTTATGGTGC

TGCATCC-3'

Antisense primer:
                                                (SEQ ID NO: 10)
5'-CCCAAGCTTCTATTATTAGTTCAAGGATGCAGCACCATAAAGTGAA

TC-3'

Sense primer:
                                                (SEQ ID NO: 11)
5'-GCTCTAGAATGACTGTGGACAACCCGGCTTCTACTACAAACAAAGA

CAAATTGTTTTCT-3'

Antisense primer:
                                                (SEQ ID NO: 12)
5'-CCCAAGCTTCTATTATTACTTCCACACAGAAAACAATTTGTCTTTG

TTTGTAGT-3'

Sense primer:
                                                (SEQ ID NO: 13)
5'-GCTCTAGACCAGGGGCACCGGTGCCAGAGAAATAAT-3'

Antisense primer:
                                                (SEQ ID NO: 14)
5'-CCCAAGCTTCTATTATTATTTCTCTGGCACCGGTGC-3'

Sense primer:
                                                (SEQ ID NO: 15)
5'-GCTCTAGACTCGCTCCCTTATCCACCAAAGACCTGACAACGTACGC

TAG-3'

Antisense primer:
                                                (SEQ ID NO: 16)
5'-CCCAAGCTTCTATTATTAGTACGTTGTCAGGTCTTTGGTGGAT-3'
```

<Target to which the Peptide Binds>

The target to which the peptide binds is not particularly limited and may be appropriately selected depending on the intended purpose. Examples thereof include a transferrin receptor.

—Transferrin Receptor—

It is known that the extracellular domain of the transferrin receptor (TfR) include, as illustrated in FIG. 4, a first protease-like domain (PD1; Protease-like domain 1), an apical domain (AD; Apical domain), a second protease-like domain (PD2; Protease-like domain 2) and a helical domain (HD; Helical domain).

Among these domains, the peptide preferably binds to AD, and the peptide more preferably binds to each of the amino acid sequences expressed by the following SEQ ID NOs: 5 to 8, or any combination thereof. Notably, the amino acid sequence expressed by the following SEQ ID NO: 5 is a sequence derived from a mouse transferrin 1 receptor. The amino acid sequence expressed by the following SEQ ID NO: 6 is a sequence derived from a human transferrin 1 receptor. The amino acid sequence expressed by the following SEQ ID NO: 7 is a sequence derived from a human transferrin 2 receptor. The amino acid sequence expressed by the following SEQ ID NO: 8 is a sequence derived from a mouse transferrin 2 receptor.

N terminus (321)-TQFPPSQSS-(329) C terminus (SEQ ID NO: 5)

N terminus (318)-TQFPPSRSS-(326) C terminus (SEQ ID NO: 6)

N terminus (341)-TQFPPVASS-(349) C terminus (SEQ ID NO: 7)

N terminus (336)-TQFPPVESS-(344) C terminus (SEQ ID NO: 8)

In addition to the function of permeating the blood-brain barrier, the peptide can bind to any cell having, for example, a receptor including each of the amino acid sequences expressed by SEQ ID NOs: 5 to 8, or any combination thereof, and is taken into the cell depending on the cell type. Also, the target to which the peptide binds is not limited to the receptor and may be appropriately selected depending on the intended purpose.

<Use>

Use of the peptide is not particularly limited and may be appropriately selected depending on the intended purpose. The peptide is suitably used in, for example, the below-described drug transporter, antipoliovirus agent, blood-brain barrier permeating agent and transferrin receptor capturing body of the present invention.

(Drug Transporter)

A drug transporter of the present invention includes at least the peptide of the present invention; and, if necessary, further includes other ingredients such as a carrier and a drug.

<Peptide>

The amount of the peptide in the drug transporter is not particularly limited and may be appropriately selected depending on the intended purpose so long as the drug transporter can transport a drug.

As described above, the peptide may consist of an amino acid sequence that is identical to each of the amino acid sequences expressed by SEQ ID NOs: 1 to 4, or any combination thereof except that one or several amino acids are substituted, deleted or added in the entirety or a part thereof. Also, the N or C terminus of the peptide may be subjected to chemical modification. The substitution, deletion or addition of the amino acids and the chemical modification in the drug transporter are not particularly limited and may be appropriately selected depending on the drug to be transported. The drug may be transported with carried on the peptide or may be transported with carried on the below-described carrier.

<Carrier>

The form of the carrier is not particularly limited and may be appropriately selected depending on the intended purpose. Examples thereof include: a form where the drug is enclosed in a closed space defined by a membrane; a form where the drug is enclosed between membranes; and a form where the drug is enclosed in a membrane. Also, the form of the carrier may be a combined form of these forms. In this manner, the carrier can have various forms and thus "carry" or "carried" has a wide variety of meanings depending on the form such as enclosure, encapsulation and interaction.

Specific examples of the form of the carrier include a macromolecule, a microassembly, a microparticle, a microsphere, a nanosphere, a liposome, and an emulsion. The carrier is not particularly limited and may be appropriately selected depending on the intended purpose from those known in the field of pharmaceutical preparations.

The average particle diameter of the drug transporter is not particularly limited and may be appropriately selected depending on the intended purpose so long as the drug transporter can be transported into a cell.

The method with which the drug transporter is taken into the cell is not particularly limited and may be appropriately selected depending on the intended purpose. Examples thereof include phagocytosis, endocytosis, pinocytosis and macropinocytosis.

Many cells are known to use endocytosis for intake. The size capable of being taken through endocytosis is up to about 300 nm. When it is equal to or larger than this size, the intake amount may be considerably reduced.

Therefore, the average particle diameter of the drug transporter is preferably less than 300 nm. The average particle diameter can be measured with a particle distribution analyzer.

<Drug>

The drug is not particularly limited and may be appropriately selected depending on the intended purpose. Examples thereof include drugs for prevention, treatment, diagnosis, or any combination thereof, and other pharmacologically acceptable, pharmacologically active substances, physiologically active substances and diagnostic substances.

The property of the drug is not particularly limited and may be appropriately selected depending on the intended purpose, but may be a hydrophilic drug or a hydrophobic drug.

The kind of the drug is not particularly limited and may be appropriately selected depending on the intended purpose. Examples thereof include: physiologically active substances such as a nucleic acid, a polynucleotide, a gene, an analog thereof, glycosaminoglycan, a derivative thereof, oligosaccharide, polysaccharide, a derivative thereof, a protein and a peptide; and pharmacologically active substances such as an antineurotic agent, an antivirus agent, an anticancer agent, an antibiotics, an enzyme drug, an antioxidant, an anti-inflammatory agent, a steroid drug, an angiotensin converting enzyme inhibitor, a vasodilating agent, an inhibitor of proliferation and/or migration of smooth muscle cells, a platelet aggregation inhibitor, an anticoagulant, a chemical mediator release inhibitor, an immunosuppressant, a lipid intake inhibitor, a hormone drug, an angiotensin receptor antagonist, an agent for proliferating or suppressing vascular endothelial cells, an aldose reductase inhibitor, a mesangial cell proliferation inhibitor, a lipoxygenase inhibitor, an immunopotentiating agent, a Maillard reaction suppressor, an amyloidosis inhibitor, a nitric oxide synthase (NOS) inhibitor, an advanced glycation endproducts (AGEs) inhibitor and a radical scavenger. These may be used alone or in combination of two or more thereof.

Since the drug transporter can suitably permeate the blood-brain barrier, the drug is preferably, among these drugs, a drug usable for treatment, diagnosis or both for the central nervous system, and is more preferably a drug capable of treating an infection with poliovirus.

Specific examples of the antineurotic agent include anxiolytic agents such as Constan, Sepazon, Cersine, Serenal, Solanax, Depas, Balance, Meilax, Rize, Rivotril, Lexotan, Wypax, Sediel, Grandaxin and Erispan; antidepressants such as Anafranil, Tofranil, Tryptanol, Amoxan, Amplit, Prothiaden, Tecipul, Tetramide, Ludiomil, Desyrel, Reslin, Abilit, Dogmatyl, Miradol, Ritalin, Depromel, Paxil, Luvox and Toledomin; sleeping drugs such as Amoban, Halcion, Evamyl, Myslee, Rhythmy, Lendormin, Loramet, Silece, Doral, Benzarin, Eurodin, Rohypnol, Insumin, Somelin, Dalmate, Phenobal and Isomytal; tranquilizers such as Wintermin, Contomin, Neuleptil, Hirnamin, PZC, Melleril, Impromen, Serenace, Orap, Cremin, Clofekton, Defekton, Forit, Lodopin and Atarax; mood stabilizers such as Limas and Tegretol; antiepileptic agents such as Ethotoin, Phenyloin, Acetylpheneturide, Primidone, Sultiame, Ethosuximide, Clonazepam, Carbamazepine, sodium valproate and Zonisamide; and Parkinson's disease therapeutic agents such as levodopa agents, pergolide mesilate, amantadine hydrochloride, trihexyphenidyl hydrochloride, piroheptine hydrochloride, mazaticol hydrochloride, metixene hydrochloride, biperiden, profenamine and droxidopa.

Specific examples of the antivirus agent include aciclovir, ganciclovir, didanosine, zidovudine, sorivudine and vidarabine.

Specific examples of the anticancer agent include cyclophosphamide, ifosfamide, nitrogen mustard N-oxide hydrochloride, thiotepa, busulfan, carboquone, nimustine hydrochloride, ranimustine, melphalan, improsulfan tosilate, dacarbazine, procarbazine hydrochloride, cytarabine, cytarabine ocfosfate, Enocitabine, mercaptopurine, thioinosine, fluorouracil, Doxifluridine, tegafur, methotrexate, Carmofur, Hydroxycarbamide, vincristine sulfate, vinblastine sulfate, vindesine sulfate, etoposide, chromomycin A3, daunorubicin hydrochloride, doxorubicin hydrochloride, aclarubicin hydrochloride, pirarubicin, epirubicin hydrochloride, dactinomycin, mitoxantrone hydrochloride, bleomycin hydrochloride, peplomycin sulfate, mitomycin C, neocarzinostatin, L-asparaginase, aceglatone mitobronitol, dextran sulfate sodium, octreotide acetate, cisplatin, carboplatin, tamoxifen citrate, medroxyprogesterone acetate, estramustine sodium phosphate, goserelin acetate and leuprorelin acetate.

Specific examples of the antibiotics include benzylpenicillin potassium, benzylpenicillin benzathine, phenoxymethylpenicillin potassium, phenethicillin potassium, cloxacillin sodium, flucloxacillin sodium, ampicillin, sultamicillin tosilate, bacampicillin hydrochloride, talampicillin hydrochloride, lenampicillin, hetacillin potassium, ciclacillin, amoxicillin, pivmecillinam hydrochloride, aspoxicillin, carbenicillin sodium, carindacillin sodium, sulbenicillin sodium, ticarcillin sodium, piperacillin sodium, cefaloridine, cefalothin sodium, cefazolin sodium, cefapirin sodium, cefradine, cefalexin, propylene glycol cefatrizine, cefroxadine, cefaclor, cefadroxil, cefotiam hydrochloride, cefotiam hexetil hydrochloride, cefuroxime sodium, cefuroxime axetil, cefamandole sodium, cefdinir, cefetamet pivoxil hydrochloride, ceftibuten, cefinetazole sodium, cefoxitin sodium, cefotetan sodium, cefminox sodium, cefbuperazone sodium, cefpiramide sodium, cefsulodin sodium, cefoperazone sodium, ceftizoxime sodium, cefinenoxime hydrochloride, ceftriaxone sodium, ceftazidime, cefpimizole sodium, cefixime, cefteram pivoxil, cefuzonam sodium, cefpodoxime proxetil, cefodizime, cefpirome sulfate, latamoxef sodium, flomoxef sodium, imipenem, cilastatin sodium, aztreonam, carumonam sodium, streptomycin sulfate, kanamycin sulfate, fradiomycin sulfate, amikacin sulfate, gentamicin sulfate, paromomycin sulfate, bekanamycin sulfate, ribostamycin sulfate, dibekacin sulfate, tobramycin, sisomicin sulfate, mithromycin sulfate, astromicin sulfate, netilmicin sulfate, isepamicin sulfate, arbekacin sulfate, erythromycin, kitasamycin, acetylkitasamycin, oleandomycin phosphate, Josamycin, acetylspiramycin, midecamycin, midecamycin acetate, rokitamycin, roxithromycin, clarithromycin, tetracycline hydrochloride, oxytetracycline hydrochloride, tetracycline metaphosphate, demethylchlortetracycline hydrochloride, rolitetracycline, doxycycline hydrochloride, minocycline hydrochloride, chloramphenicol, chloramphenicol sodium succinate, chloramphenicol palmitate, thiamphenicol, thiamphenicol aminoacetate hydrochloride, colistin sulfate, colistin sodium methanesulfonate, polymyxin B sulfate, Bacitracin, vancomycin hydrochloride, lincomycin hydrochloride, clindamycin, spectinomycin hydrochloride and fosfomycin calcium.

Specific examples of the enzyme drug include chymotrypsin, crystallized trypsin, streptokinase-streptodornase, hyaluronidase, urokinase, nasaruplase, alteplase, lysozyme chloride, semi-alkaline proteinase, serrapeptase, tisokinase, duteplase, batroxobin, pronase and bromelain.

Specific examples of the antioxidant include tocopherol, ascorbic acid and uric acid.

Specific examples of the anti-inflammatory agent include choline salicylate, sasapyrine, sodium salicylate, aspirin, diflunisal, flufenamic acid, mefenamic acid, floctafenine, tolfenamic acid, diclofenac sodium, tolmetin sodium, sulindac, fenbufen, felbinac ethyl, indomethacin, indometacin farnesil, acemetacin, proglumetacin maleate, amfenac sodium, nabumetone, ibuprofen, flurbiprofen, flurbiprofen axetil, ketoprofen, naproxen, protizinic acid, pranoprofen, fenoprofen calcium, tiaprofenic acid, oxaprozin, loxoprofen sodium, alminoprofen, zaltoprofen, phenylbutazone, clofezone, ketophenylbutazone, piroxicam, tenoxicam, ampiroxicam, tiaramide hydrochloride, tinoridine hydrochloride, benzydamine hydrochloride, epirizole and emorfazone.

Specific examples of the steroid drug include cortisone acetate, hydrocortisone (phosphate ester, acetic acid salt), hydrocortisone butyrate, hydrocortisone sodium succinate, prednisolone (acetate, succinate, tertially butyl acetate ester, phosphate ester), methylprednisolone (acetate), sodium methylprednisolone succinate, triamcinolone, triamcinolone acetonide (triamcinolone acetate), dexamethasone (phosphate ester, acetic acid salt, phosphoric acid sodium salt, sulfate ester), dexamethasone palmitate, betamethasone (phosphoric acid salt, 2 sodium salt), paramethasone acetate, fludrocortisone acetate, halopredone acetate, clobetasol propionate, halcinonide, beclometasone dipropionate, betamethasone valerate, betamethasone acetate and cortisone acetate.

Specific examples of the angiotensin converting enzyme inhibitor include alacepril, imidapril hydrochloride, temocapril hydrochloride, delapril hydrochloride, benazepril hydrochloride, captopril, cilazapril, enalapril maleate and lisinopril.

Specific examples of the vasodilating agent include theophylline, diprophylline, proxyphylline, aminophylline, choline theophylline, prostaglandin, prostaglandin derivatives, alprostadil alfadex, alprostadil, limaprost alfadex, papaverine, cyclandelate, cinnarizine, bencyclane fumarate, cinepazide maleate, dilazep hydrochloride, trapidil, difenidol hydrochloride, nicotinic acid, inositol hexanicotinate, nicametate citrate, nicotinyl alcohol tartrate, tocopherol nicotinate, hepronicate, isoxsuprine hydrochloride, bamethan sulfate, tolazoline hydrochloride, dihydroergotoxine mesylate, ifenprodil tartrate, moxisylyte hydrochloride, nicergoline, nicardipine hydrochloride, nilvadipine, nifedipine, benidipine hydrochloride, diltiazem hydrochloride, nisoldipine, nitrendipine, manidipine hydrochloride, barnidipine hydrochloride, efonidipine hydrochloride, verapamil hydrochloride, trimetazidine hydrochloride, captopril, enalapril maleate, alacepril, delapril hydrochloride, cilazapril, lisinopril, benazepril hydrochloride, hydralazine hydrochloride, todralazine hydrochloride, budralazine, cadralazine, indapamide, carbocromen hydrochloride, efloxate, etafenone hydrochloride, oxyfedrine hydrochloride, nicorandil, amyl nitrite and isosorbide dinitrate.

Specific examples of the inhibitor of proliferation and/or migration of smooth muscle cells include heparin sodium, dalteparin sodium (low-molecular-weight heparin), heparin calcium and dextran sulfate.

Specific examples of the platelet aggregation inhibitor include ticlopidine hydrochloride, cilostazol, ethyl icosapentate, beraprost sodium, sarpogrelate hydrochloride, batroxobin and dipyridamole.

Specific examples of the anticoagulant include heparin sodium, dalteparin sodium (low-molecular-weight heparin), heparin calcium, dextran sulfate, warfarin potassium and argatroban.

Specific examples of the chemical mediator release inhibitor include tranilast, ketotifen fumarate, azelastine hydrochloride, oxatomide, amlexanox and repirinast.

Specific examples of the immunosuppressant include cicrosporin.

The drug used for diagnosis is not particularly limited and may be appropriately selected depending on the intended purpose. Examples thereof include X-ray contrast agents, radioisotope label nuclear medicine diagnostic drugs and nuclear magnetic resonance diagnostic drugs.

Specific examples of the X-ray contrast agents include meglumine amidotrizoate, sodium iotalamate, meglumine iotalamate, gastrografin, meglumine iodamide, lipiodol ultra fluide, adipiodone meglumine, ioxaglic acid, meglumine iotroxate, iotrolan, iopanoic acid, iopamidol, iohexyl, iversol, sodium iopodate, iomeprol, isopaque and iodoxamic acid.

The amount of the drug carried on the drug transporter is not particularly limited and may be appropriately selected depending on, for example, the type of the drug.

<Other Ingredients>

The other ingredients in the drug transporter are not particularly limited and may be appropriately selected depending on the intended purpose. Examples thereof include additives, supplements and water. These may be used alone or in combination of two or more thereof.

The additives or supplements are not particularly limited and may be appropriately selected depending on the intended purpose. Examples thereof include a disinfectant, a preserving agent, a binding agent, a thickener, an adhesive agent, an integrating agent, a colorant, a stabilizer, a pH adjuster, a buffer, a tonicity agent, a solvent, an antioxidant, a UV rays-preventing agent, a preventing agent for precipitation of crystals, a defoaming agent, a property improving agent and an antiseptic agent.

The other ingredients may be formulated together with the drug transporter or formulated in the carrier.

The disinfectant is not particularly limited and may be appropriately selected depending on the intended purpose. Examples thereof include cationic surfactants such as benzalkonium chloride, benzethonium chloride and cetylpyridinium chloride.

The preserving agent is not particularly limited and may be appropriately selected depending on the intended purpose. Examples thereof include p-hydroxybenzoate esters, chlorobutanol and clesol.

The binding agent, thickener and adhesive agent are not particularly limited and may be appropriately selected depending on the intended purpose. Examples thereof include starch, dextrin, cellulose, methyl cellulose, ethyl cellulose, carboxymethyl cellulose, hydroxyethyl cellulose, hydroxypropyol cellulose, hydroxypropyolmethyl cellulose, carboxymethyl starch, pullulan, sodium alginate, ammonium alginate, propylene glycol alginic acid esters, guar gum, locust bean gum, gum Arabic, xanthane gum, gelatin, casein, polyvinyl alcohol, polyethylene oxide, polyethylene glycol, ethylene/propylene block polymers, sodium polyacrylates and polyvinylpyrrolidone. These may be used alone or in combination of two or more thereof.

The integrating agent is not particularly limited and may be appropriately selected depending on the intended purpose. Examples of the integrating agent include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate and polyvinylpyrrolidone.

The colorant is not particularly limited and may be appropriately selected depending on the intended purpose. Examples thereof include titanium oxide and iron oxide.

The stabilizer is not particularly limited and may be appropriately selected depending on the intended purpose. Examples thereof include tragacanth, gum Arabic, gelatin, sodium pyrosulfite, EDTA, thioglycolic acid and thiolactic acid.

The pH adjuster and the buffer are not particularly limited and may be appropriately selected depending on the intended purpose. Examples thereof include sodium citrate, sodium acetate and sodium phosphate.

The tonicity agent is not particularly limited and may be appropriately selected depending on the intended purpose. Examples thereof include sodium chloride and glucose.

The amount of the other ingredients in the drug transporter is not particularly limited and may be appropriately selected depending on the intended purpose.

<Transportation of the Drug Transporter>

The method for transporting the drug transporter into a cell is not particularly limited and may be appropriately selected depending on the intended purpose. Examples thereof include methods using functions or properties of cells into which the drug transporter is to be transported.

Examples of the functions or properties of cells usable for the transportation of the drug transporter include phagocytosis and endocytosis of cells.

Prior to administration of the drug transporter, cells may be activated in advance to cause phagocytosis or endocytosis. When cells are excessively activated to increase their adhesiveness or cause aggregation, they may be inactivated with an appropriately selected method.

The cells to which the drug transporter can be applied are not particularly limited and may be appropriately selected depending on the intended purpose so long as the cells can recognize each of the amino acid sequences expressed by the above SEQ ID NOs: 1 to 4, or any combination thereof. Since the peptide of the present invention can permeate the blood-brain barrier; i.e., the drug transporter can permeate the blood-brain barrier, it can suitably be used for, for example, prevention, treatment or diagnosis of the central nervous system.

The cells constituting the central nervous system are not particularly limited and may be appropriately selected depending on the intended purpose. Examples thereof include nerve cells, glial cells, vascular endothelial cells and pericytes. Among them, the drug transporter is suitably transported into vascular endothelial cells.

<Administration>

The administration method, administration dose, administration period and administration target of the drug transporter are not particularly limited and may be appropriately selected depending on the intended purpose.

The administration method is not particularly limited and may be appropriately selected depending on the intended purpose. Examples thereof include a local administration method, an enteral administration method and a parenteral administration method.

The local administration method is not particularly limited and may be appropriately selected depending on the intended purpose. Examples thereof include an epicutaneous administration method, an inhalation administration method, an infusion administration method, a method of administering eye drops on the conjunctiva, an intranasal administration method and an intravaginal administration method.

The enteral administration method is not particularly limited and may be appropriately selected depending on the intended purpose. Examples thereof include a peroral administration method, a tube feeding method and an enema administration method.

The parenteral administration method is not particularly limited and may be appropriately selected depending on the intended purpose. Examples thereof include an intravenous administration method, an intra-arterial administration method, an intramuscular administration method, an intracardiac administration method, a subcutaneous administration method, an intraosseous administration method, an intracutaneous administration method, an intrathecal administration method, an intraperitoneal administration method, an intravesical administration method, a percutaneous administration method, a mucosal administration method, an inhalation administration method, an epidural administration method and an intravitreal administration method.

The administration dose is not particularly limited and may be appropriately selected considering various factors of an administration target, such as the age, body weight, constitution, symptom and the presence or absence of administration of a drug containing other active ingredients.

The animal species serving as the administration target is not particularly limited and may be appropriately selected depending on the intended purpose. Examples thereof include human, monkey, pig, bovine, sheep, goat, dog, cat, mouse, rat and bird, with human being suitably used.

<Use>

The drug transporter may be used alone or in combination with a drug or a drug transporter containing other active ingredients. Also, the drug transporter may be formulated into a drug containing other active ingredients before use.

<Application>

Since the drug transporter of the present invention can permeate the blood-brain barrier, the drug transporter can suitably be used for prevention, treatment or diagnosis of disorders in the central nervous system. In particular, it is suitably used for prevention, treatment or diagnosis of infections with poliovirus.

(Antipoliovirus Agent and Blood-Brain Barrier Permeating Agent)

<Antipoliovirus Agent>

An antipoliovirus agent of the present invention contains the peptide of the present invention; and, if necessary, further contains other ingredients.

The antipoliovirus agent can suitably bind to a transferrin receptor as a receptor for poliovirus present on vascular endothelial cells of the central nervous system, especially vascular endothelial cells constituting the blood-brain barrier. When the antipoliovirus agent binds to the transferrin receptor, the antipoliovirus agent is taken in the vascular endothelial cells having the transferrin receptor by the action of, for example, endocytosis. As a result, the antipoliovirus agent has a competitive inhibitory effect against permeation of poliovirus through the blood-brain barrier, and can prevent permeation of poliovirus through the blood-brain barrier to prevent neural disorders accompanied by infection with poliovirus.

The amount of the peptide in the antipoliovirus agent is not particularly limited and may be appropriately selected depending on the intended purpose so long as the antipoliovirus agent can prevent permeation of poliovirus through the blood-brain barrier. Also, the antipoliovirus agent may be the peptide itself.

<Blood-Brain Barrier Permeating Agent>

The blood-brain barrier permeating agent of the present invention contains the peptide of the present invention; and, if necessary, further contains other ingredients.

The amount of the peptide in the blood-brain barrier permeating agent is not particularly limited and may be appropriately selected depending on the intended purpose so long as the blood-brain barrier permeating agent can permeate the blood-brain barrier. Also, the blood-brain barrier permeating agent may be the peptide itself.

<Other Ingredients>

The other ingredients in the antipoliovirus agent or the blood-brain barrier permeating agent are not particularly limited and may be appropriately selected depending on the intended purpose. Examples thereof include pharmacologically acceptable carriers.

The above carriers are also not particularly limited and may be appropriately selected depending on, for example, the dosage form of the antipoliovirus agent. Examples thereof include those described above as the other ingredients in the drug transporter.

The amount of the other ingredients in the antipoliovirus agent or the blood-brain barrier permeating agent is not particularly limited and may be appropriately selected depending on the intended purpose.

The antipoliovirus agent or the blood-brain barrier permeating agent may be used alone or in combination of two or more thereof. The antipoliovirus agent or the blood-brain barrier permeating agent may be used in combination with a drug containing other active ingredients. Also, the antipoliovirus agent or the blood-brain barrier permeating agent may be formulated into a drug containing other active ingredients before use.

<Dosage Form>

The dosage form of the antipoliovirus agent or the blood-brain barrier permeating agent is not particularly limited and may be appropriately selected depending on the intended administration method. Examples thereof include a solid preparation, a semi-solid preparation and a liquid preparation.

The method for producing the antipoliovirus agent or the blood-brain barrier permeating agent is not particularly limited and may be appropriately selected from routine method depending on the dosage form.

—Solid Preparation—

The solid preparation is not particularly limited and may be appropriately selected depending on the intended purpose. When it is used as an internal preparation, examples of the solid preparation include tablets, chewable tablets, foaming tablets, orally-disintegrating tablets, troches, drops, hard capsules, soft capsules, granules, powder, pills, dry syrups and infusions.

When the solid preparation is an external preparation, examples of the solid preparation include suppositories, cataplasms and plasters.

—Semi-Solid Preparation—

The semi-solid preparation is not particularly limited and may be appropriately selected depending on the intended purpose. When it is used as an internal preparation, examples of the semi-solid preparation include electuaries, chewing gums, whip and jelly.

When the semi-solid preparation is used as an external preparation, examples of the semi-solid preparation include ointments, cream, mousse, inhaler and nasal gel.

—Liquid Preparation—

The liquid preparation is not particularly limited and may be appropriately selected depending on the intended purpose. When it is used as an internal preparation, examples of the liquid preparation include syrups, drinks, suspensions and spirits.

When the liquid preparation is used as an external preparation, examples of the liquid preparation include liquid, eye drops, aerosol and sprays.

<Administration>

The administration method, administration dose, administration period and administration target of the drug transporter are not particularly limited and may be appropriately selected depending on the intended purpose.

The administration method is not particularly limited and may be appropriately selected depending on the intended purpose. Examples thereof include a local administration method, an enteral administration method and a parenteral administration method.

The administration dose is not particularly limited and may be appropriately selected considering various factors of an administration target, such as the age, body weight, constitution, symptom and the presence or absence of administration of a drug containing other active ingredients.

The animal species serving as the administration target is not particularly limited and may be appropriately selected depending on the intended purpose. Examples thereof include human, monkey, pig, bovine, sheep, goat, dog, cat, mouse, rat and bird, with human being suitably used.

(Transferrin Receptor Capturing Body)

A transferrin receptor capturing body of the present invention contains the peptide of the present invention; and, if necessary, further contains other ingredients. The transferrin receptor capturing body can suitably capture transferrin.

The amount of the peptide in the transferrin receptor capturing body is not particularly limited and may be appropriately selected depending on the intended purpose so long as the transferrin receptor capturing body can capture a transferrin receptor. Also, the transferrin receptor capturing body may be the peptide itself.

<Other Ingredients>

The other ingredients in the transferrin receptor capturing body are not particularly limited and may be appropriately selected depending on the intended purpose. Examples thereof include pharmacologically acceptable carriers.

The above carriers are also not particularly limited and may be appropriately selected depending on the intended purpose. Examples thereof include those described above as the other ingredients in the drug transporter.

The amount of the other ingredients in the transferrin receptor capturing body is not particularly limited and may be appropriately selected depending on the intended purpose.

The transferrin receptor capturing body may be used alone or in combination of two or more thereof. The transferrin receptor capturing body may be used in combination with a drug containing other active ingredients. Also, the transferrin receptor capturing body may be formulated into a drug containing other active ingredients before use.

EXAMPLES

The present invention will next be described in detail by way of Examples, which should not be construed as limiting the present invention thereto.

Test Example 1

Effects of Transferrin on Permeation of Poliovirus Through the Blood-Brain Barrier —Preparation of Brain Capillary Endothelial Cells—

Mouse brain capillary endothelial cells (MBEC) 4 were cultured in D-MEM (product of Sigma Co., Ltd.) containing 10% by mass inactivated fetal bovine serum (FBS) (product of COSMO BIO Co., Ltd.).

These brain capillary endothelial cells were dispersed by treating them with tripsin-EDTA (ethylene diaminetetraacetate).

Note that, the MBEC had been prepared according to the description of Shirai A et al., BBA; 1994 Jul. 21; 1222(3): 400-404.

—Preparation of Poliovirus—

Purified poliovirus (PV) was prepared according to the description of Yang W X. et al., 1997, Virology, Vol. 229, p. 421-p. 428 previously reported by the present inventors.

Floating HeLa cells infected with poliovirus (Mahoney strain) were homogenized with a Dounce-type homogenizer in a buffer (10 mM Tris-HCL (pH 7.4), 100 mM sodium chloride, 1.5 mM magnesium chloride, 5 mM EDTA). The cytoplasm fraction was treated with DEAE-Sepharose (trade name: CL-6B, product of GE Healthcare, Co., Ltd.) and subjected to sucrose density-gradient centrifugation and cesium chloride density-gradient centrifugation. After that, the resultant product was treated with a desalting column (trade name: PD-10, GE Healthcare, Co., Ltd.) to purify poliovirus particles.

—Preparation of Fluorescence-Labeled Poliovirus—

The above-purified poliovirus was fluorescence-labeled with the following: trade name: Alexa Fluor (registered trademark) 568-Protein Labeling Kit (product of Invitrogen Co., Ltd.). The fluorescence-labeled poliovirus was prepared in PBS so as to have a concentration of 0.4 mg/mL.

Note that, the composition of the PBS is as follows: 2.7 mM potassium chloride, 1.47 mM potassium dihydrogenphosphate (anhydrous), 137 mM sodium chloride, and 8.1 mM sodium monohydrogen phosphate (anhydrous).

<Blood-Brain Barrier Permeation Test of Poliovirus>

A Transwell plate (trade name, product of Corning Incorporated (12 wells)) was coated with I-type collagen (product of Sigma Co., Ltd.) at 37° C. for 4 hours and dried overnight before use.

The above-prepared brain capillary endothelial cells were placed on the upper layer portion of the Transwell plate at $7 \times 10^4$ cells/well, and cultured for 72 hours at 37° C. and 5% $CO_2$ in D-MEM (product of Sigma Co., Ltd.) containing 10% by mass inactivated fetal bovine serum (FBS) (product of COSMO BIO Co., Ltd.), to thereby establish an in vitro model culture system of the blood-brain barrier.

The fluorescence-labeled poliovirus (127 μg/mL) and fluorescence-labeled transferrin (trade name: Alexa Fluor (registered trademark) 555-transferrin, product of Invitrogen Co., Ltd.) (180 μg/mL) or FITC-labeled dextran (product of Sigma Co., Ltd.) (180 μg/mL) were added to the culture of the brain capillary endothelial cells in the Transwell plate. At 5 min, 10 min and 15 min after that, the culture in the lower layer portion of the Transwell plate was recovered and measured for fluorescence intensity with a spectrofluoro-photometer (trade name: F-2500, product of Hitachi High-Technologies Corporation). The fluorescence intensity was indicated as a permeation amount of poliovirus through the brain capillary endothelial cells in the Transwell plate.

The results are presented in FIG. 1. In the case where only poliovirus was added (corresponding to "PV" in FIG. 1), the PS value (permeation rate, permeation activity) was 1.89. In the case where poliovirus and transferrin were added (corresponding to "PV+Tf" in FIG. 1), the PS value was 1.02. In the case where dextran was added, the PS value was 0.20.

Since the permeation rate was lower in the case of (PV+Tf) where poliovirus and transferrin were mixed and added to the brain capillary endothelial cells than in the case of (PV) where poliovirus was added alone to the brain capillary endothelial cells, it was found that transferrin inhibits the permeation of poliovirus through the blood-brain barrier. This result suggests that poliovirus permeates the brain capillary endothelial cells via a receptor common to that for transferrin.

Test Example 2

Confirmation of Binding Between Poliovirus and Transferrin Receptor

Next, whether the poliovirus directly bound to a transferrin receptor was confirmed by western blotting in the following manner. FIG. 2 is a schematic, explanatory representation of Test Example 2.

—Preparation of a Transferrin Receptor—

—Cloning of Mouse Transferrin Receptor 1 (mTfR1)—

Total RNA, which had been prepared from the liver of a mouse, was used to prepare cDNA with PtimeScript 1st Strand cDNA synthesis Kit (product of TAKARA BIO INC.). The prepared cDNA was used as a template for cloning of mTfR1 soluble domain (R123 to F763). Based on the sequence of GeneBank registration number BC054522.1, the following primers were designed and used: a sense primer with a primer sequence expressed by the following SEQ ID NO: 17 containing a SacII cutting site (underlined sequence); and an antisense primer with a primer sequence expressed by the following SEQ ID NO: 18 containing a XhoI cutting site (underlined sequence) (downstream by 150 bases from the termination codon on the 3' side). PCR was performed using these primers to amplify a gene fragment of mTfR1. The gene fragment was inserted into a SacII-XhoI cutting site of an expression vector for an N terminus Strep tag-fused protein (trade name: pASK-IBA7(+), product of IBA Co., Ltd.). The thus-constructed expression vector may be referred to as pASK-mTfR1, hereinafter.

```
Sense primer:
                                    (SEQ ID NO: 17)
5'-TCCCCGCGGTCGCTTATATTGGGCAGACCTCAAA-3'

Antisense primer:
                                    (SEQ ID NO: 18)
5'-CCGCTCGAGTCCAACCCCGCACTAAAAGCTG-3'
```

—Expression and Purification of Strep-mTfR1—

The constructed expression vector pASK-mTfR1 was used to transform *Escherichia coli* JM109 (product of TOYOBO CO., LTD.), which was cultured at 37° C. until the turbidity at OD600 reached 0.5. After that, tetracycline was added to the culture at 200 ng/mL, and the cells were harvested at 3 hours after introduction of mTfR1. The harvested cells were washed with a STD buffer (20 mM Hepes-KOH (pH 7.4), 150 mM sodium chloride). The cells suspended in the STD buffer were ultrasonically disrupted for 20 sec 10 times (interval: 30 sec), followed by centrifuging at 10,000×g and 4° C. for 15 min. The centrifuged product from which undisrupted cells had been removed was used as a lysate (supernatant). Purified Strep-mTfR1 was prepared by subjecting the resultant supernatant to affinity purification using a column (trade name: Strep-tactin supper-flow sepharose column, product of IBA Co., Ltd.) and gel filtration (trade name: NAP-10 column, GE Healthcare, Co., Ltd.).

—Preparation of Live Poliovirus—

AGMK (African green monkey kidney) cells, which had been cultured in D-MEM containing 5% by mass newborn calf serum (NCS), were infected with poliovirus (Mahoney strain), and live poliovirus was prepared from the culture supernatant of the AGMK cells. This live poliovirus was found to have a virus titer of $10^8$ pfu/mL.

—Preparation of Mixture 2-1—

The live poliovirus (150 μL) and the Strep-mTfR1 (10 μg) were mixed together in the STD buffer so that the total amount of the mixture was 0.25 mL. The resultant mixture was incubated at 37° C. for 2 hours and then at 4° C. for 16 hours.

—Preparation of Mixture 2-2—

Mixture 2-2 was prepared in the same manner as in the preparation of the mixture 2-1 except that the Strep-mTfR1 was not added.

—Preparation of Mixture 2-3—

Mixture 2-3 was prepared in the same manner as in the preparation of the mixture 2-1 except that the Strep-mTfR1 was changed to Strep-tagII (product of IBA Co., Ltd.).

<Binding Test Between Poliovirus and Transferrin Receptor>

Each of the mixtures 2-1 to 2-3 was added to Strep-Tactin (registered trademark) Sepharose (Super flow) (product of IBA Co., Ltd.), followed by incubating at 4° C. for 1 hour. The resultant mixture was centrifuged at 900 rpm for 3 min and the supernatant was discarded. 200 μL of the STD buffer was added to the precipitate, and the mixture was centrifuged at 900 rpm for 3 min to wash the precipitate. This washing treatment was performed 5 times in total for purification. As a result of this purification, some compounds binding to the Strep-Tactin (registered trademark) Sepharose (Super flow) (compounds having and/or binding to the Strep-tag) remained in the precipitate, and some compounds not binding thereto were washed out.

After purification, 8 μL of 5 mM Desthiobiotin (product of Sigma Co., Ltd.) suspended in the STD buffer was added to the obtained precipitate, and the mixture was centrifuged at 900 rpm for 3 min to obtain the supernatant. This treatment releases the bond between the Strep-Tactin (registered trademark) Sepharose (Super flow) and the compound binding to the Strep-Tactin (registered trademark) Sepharose, allowing it to flow into the supernatant.

5× Sample buffer for SDS-PAGE was added to the supernatant of each of the purified mixtures 2-1 to 2-3. Also, as a positive control, 25 μL of the unpurified mixture 2-1 was sampled (10% by mass of the total amount of the mixture) and 5× sample buffer for SDS-PAGE was added thereto. These mixtures were incubated at 95° C. for 3 min and then centrifuged at 900 rpm for 3 min, and the supernatants were used as samples for SDS-PAGE.

Note that, the composition of the 5× sample buffer for SDS-PAGE is as follows: 0.312M Tris-HCl (pH 6.8), 5% by mass sodium dodecyl sulfate (SDS), 50% by mass glycerol, 0.025% by mass bromophenol blue (BPB) and 5 mM ithiothreitol (DTT). Also in the following Test Examples, the same 5× sample buffer for SDS-PAGE was used.

These samples were subjected to SDS-PAGE and western blotting according to routine methods. The western blotting was performed using, as a primary antibody, an anti-poliovirus particles antibody (trade name: rabbit polyclonal antibody) or an anti-bovine antibody (trade name: Anti Serum albumin, mouse monoclonal antibody, product of ANTIBODY SHOP Co., Ltd.) and, as a secondary antibody, an anti-rabbit Ig-HRP antibody (trade name: Anti-Rabbit Ig-HRP, product of DAKO Co., Ltd.).

The results are presented in FIG. 3. In the case of the mixture 2-1 containing poliovirus and Strep-mTfR1, bands were detected even after purification. This result indicates that poliovirus directly binds to the transferrin receptor.

Test Example 3

Identification of Binding Domain of the Transferrin Receptor to Poliovirus

Next, the following method was employed to confirm a domain of the transferrin receptor to which poliovirus binds.

Figure 4:
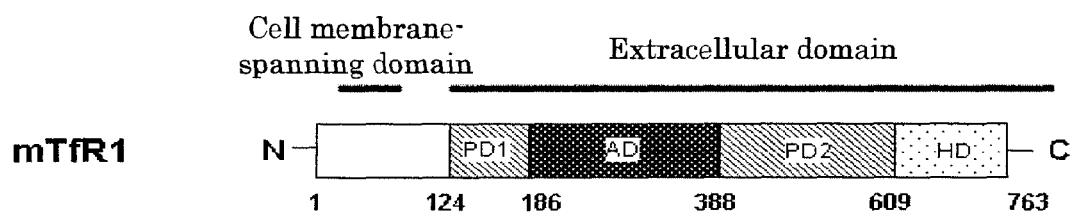

As illustrated in FIG. 4, the mouse transferrin receptor 1 (mTfR1) is known to contain: a first protease-like domain (PD1) of the $124^{th}$ residue to the $185^{th}$ residue from the N terminus side; an apical domain (AD) of the $186^{th}$ residue to $387^{th}$ residue; a second protease-like domain (PD2) of the $388^{th}$ residue to the $608^{th}$ residue; and a helical domain (HD) of the $609^{th}$ residue to the $763^{rd}$ residue. These domains are extracellular domains.

Figure 5:
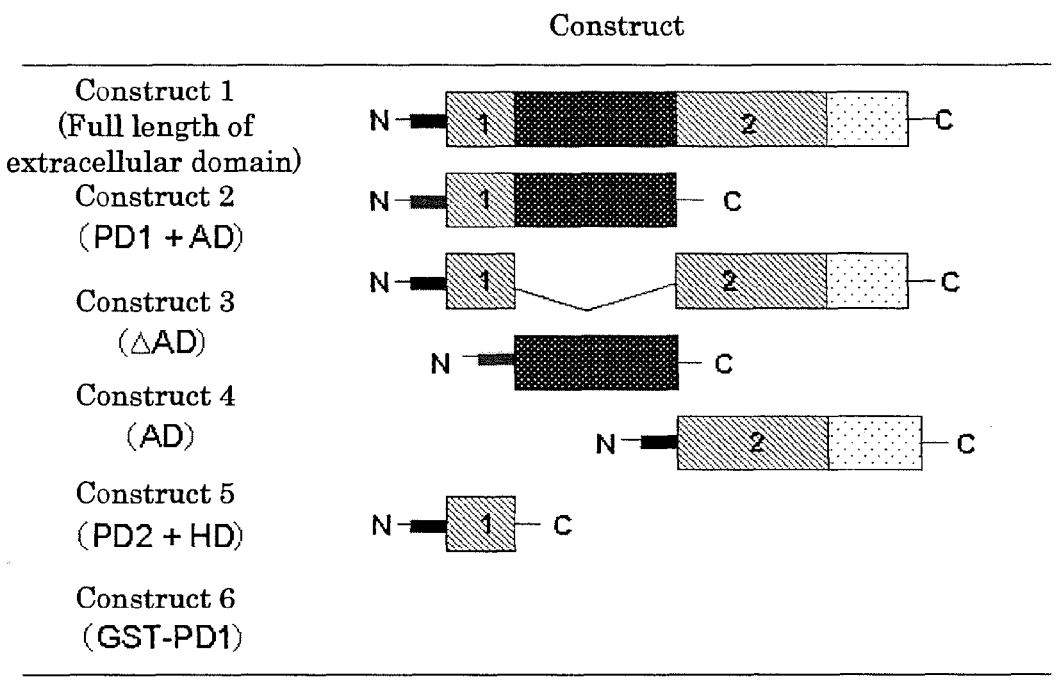

Using the pASK-mTfR1 prepared in Test Example 2 as a template for PCR, the following 6 kinds of constructs were produced by a routine method: construct 1 of the full length of the extracellular domain; construct 2 of PD1 and AD; construct 3 of the full length of the extracellular domain with AD removed (ΔAD); construct 4 of AD only; construct 5 of PD2 and HD; and construct 6 of PD1 only. FIG. 5 schematically illustrates the constructs 1 to 6.

Each of the produced constructs 1 to 5 was cloned in a Strep-tag expression vector (trade name: pASK-IBA7(+), product of IBA Co., Ltd.). The construct 6 was cloned in a GST-tag expression vector (trade name: pGEX-p4X, product of Promega Co., Ltd.).

Hereinafter, the expression vector containing the construct 1 may be referred to as "pASK-construct 1," the expression vector containing the construct 2 may be referred to as "pASK-construct 2," the expression vector containing the construct 3 may be referred to as "pASK-construct 3," the expression vector containing the construct 4 may be referred to as "pASK-construct 4," the expression vector containing the construct 5 may be referred to as "pASK-construct 5" and the expression vector containing the construct 6 may be referred to as "pGEX-construct 6."

Next, the pASK-construct 1 was introduced into *Escherichia coli* JM109 (product of TOYOBO CO., LTD.) where recombinant protein 1 (the full length of the extracellular domain) was expressed.

Similar to the case of the pASK-construct 1, the pASK-construct 2 was used to express recombinant protein 2 (PD1+AD), the pASK-construct 3 was used to express recombinant protein 3 (ΔAD), the pASK-construct 4 was used to express recombinant protein 4 (AD), the pASK-construct 5 was used to express recombinant protein 5 (PD2+HD) and the pGEX-construct 6 was used to express recombinant protein 6 (GST-PD1).

The live poliovirus (150 μL) prepared in Test Example 2, each (10 μg) of the recombinant proteins 1 to 6 and the STD buffer were mixed together so that the total amount of the mixture was 0.3 mL, and the resultant mixture was incubated at 37° C. for 2 hours and then 4° C. for 16 hours.

These mixtures were used in the same manner as in Test Example 2 to prepare samples for SDS-PAGE, which were subjected to SDS-PAGE and western blotting in the same manner as in Test Example 2.

The results are presented in the following Table 1. In Table 1, "A" refers to samples where the recombinant protein and the poliovirus were bound to each other (where a band was detected by western blotting) and "B" refers to samples where the recombinant protein and the poliovirus were not bound to each other (where no band was detected by western blotting).

The results of Table 1 indicate that poliovirus binds to the AD of the transferrin receptor. Note that, other ligands known to bind to a transferrin receptor such as transferrin have been reported to bind to PD2+HD (see Cheng Y et al., 2004, Cell, 116:565-576). Thus, the site to which poliovirus binds was different from the site to which those known ligands bind.

TABLE 1

| Recombinant protein | Domain | Bond to poliovirus |
|---|---|---|
| 1 | Full length of the extracellular domain | A |
| 2 | PD1 + AD | A |
| 3 | ΔAD | B |
| 4 | AD | A |
| 5 | PD2 + HD | B |
| 6 | PD1 | B |

Test Example 4-1

Identification of Binding Site of Poliovirus in the Transferrin Receptor

Figure 6:
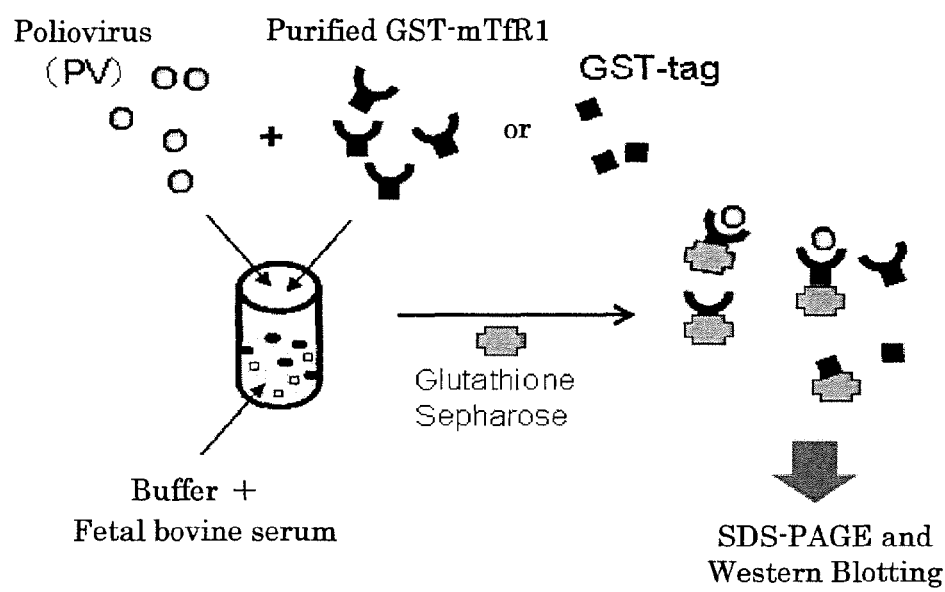

Binding capability between poliovirus and mouse transferrin receptor 1 (mTfR1) was studied by western blotting. FIG. 6 is a schematic, explanatory representation for studies by western blotting in Test Example 4-1.

—Preparation of GST-mTfR1—

An amino acid sequence expressed by the following SEQ ID NO: 5 is a partial sequence of mouse transferrin receptor 1 (mTfR1). The amino acid sequence expressed by the SEQ ID NO: 5 was cloned in a GST-tag expression vector (trade name: pGEX-p4X, product of Promega Co., Ltd.). The resultant product was used in the same manner as in Test Example 3 to prepare a GST-fused recombinant protein (hereinafter may be referred to as "GST-mTfR1").

```
                                        (SEQ ID NO: 5)
            321-TQFPPSQSS-329
```

—Preparation of Mixture 4-1—

The live poliovirus (150 μL) prepared in Test Example 2, the GST-mTfR1 (10 μg) and the STD buffer were mixed together so that the total amount of the mixture was 0.2 mL. The resultant mixture was incubated at 37° C. for 2 hours and then at 4° C. for 16 hours.

—Preparation of Mixture 4-2—

Mixture 4-2 was prepared in the same manner as in the preparation of the mixture 4-1 except that the GST-mTfR1 was changed to GST-tag (product of Promega Co., Ltd.).

—Preparation of Mixture 4-3—

Mixture 4-3 was prepared in the same manner as in the preparation of the mixture 4-1 except that poliovirus was not added.

—Preparation of Mixture 4-4—

Mixture 4-4 was prepared in the same manner as in the preparation of the mixture 4-1 except that the GST-mTfR1 was not added.

—Preparation of Mixture 4-5—

Mixture 4-5 was prepared in the same manner as in the preparation of the mixture 4-1 except that the GST-mTfR1 was changed to the Strep-mTfR1 prepared in Test Example 2.

<Binding Test Between Transferrin Receptor and Poliovirus>

Each of the mixtures 4-1 to 4-4 was added to Glutathione-Sepharose (fast-flow) (product of GE Healthcare, Co., Ltd.), followed by incubating at 4° C. for 1 hour. The resultant mixture was centrifuged at 900 rpm for 3 min and the supernatant was discarded. 200 μL of the STD buffer was added to the precipitate, and the mixture was centrifuged at 900 rpm for 3 min to wash the precipitate. This washing treatment was performed 5 times in total for purification. As a result of this purification, some compounds binding to the Glutathione-Sepharose (compounds having and/or binding to the GST-tag) remained in the precipitate, and some compounds not binding thereto were washed out.

After purification, 8 μL of 10 mM glutathione suspended in the STD buffer was added to the obtained precipitate, and the mixture was centrifuged at 900 rpm for 3 min to obtain the supernatant. This treatment releases the bond between the Glutathione-Sepharose and the compound binding to the Glutathione-Sepharose, allowing it to flow into the supernatant.

The mixture 4-5 was added to Strep-Tactin (registered trademark) Sepharose (Super flow) (product of IBA Co., Ltd.), followed by incubating at 4° C. for 1 hour. The resultant mixture was centrifuged at 900 rpm for 3 min and the supernatant was discarded. 200 μL of the STD buffer was added to the precipitate, and the mixture was centrifuged at 900 rpm for 3 min to wash the precipitate. This washing treatment was performed 5 times in total for purification.

After purification, 8 μL of 5 mM Desthiobiotin (product of Sigma Co., Ltd.) suspended in the STD buffer was added to the obtained precipitate, and the mixture was centrifuged at 900 rpm for 3 min to obtain the supernatant.

The supernatants of the purified mixtures 4-1 to 4-5 and the unpurified mixture 4-1 were treated in the same manner as in Test Example 2 to prepare samples for SDS-PAGE, which were subjected to SDS-PAGE and western blotting in the same manner as in Test Example 2.

Figures 1, 7:
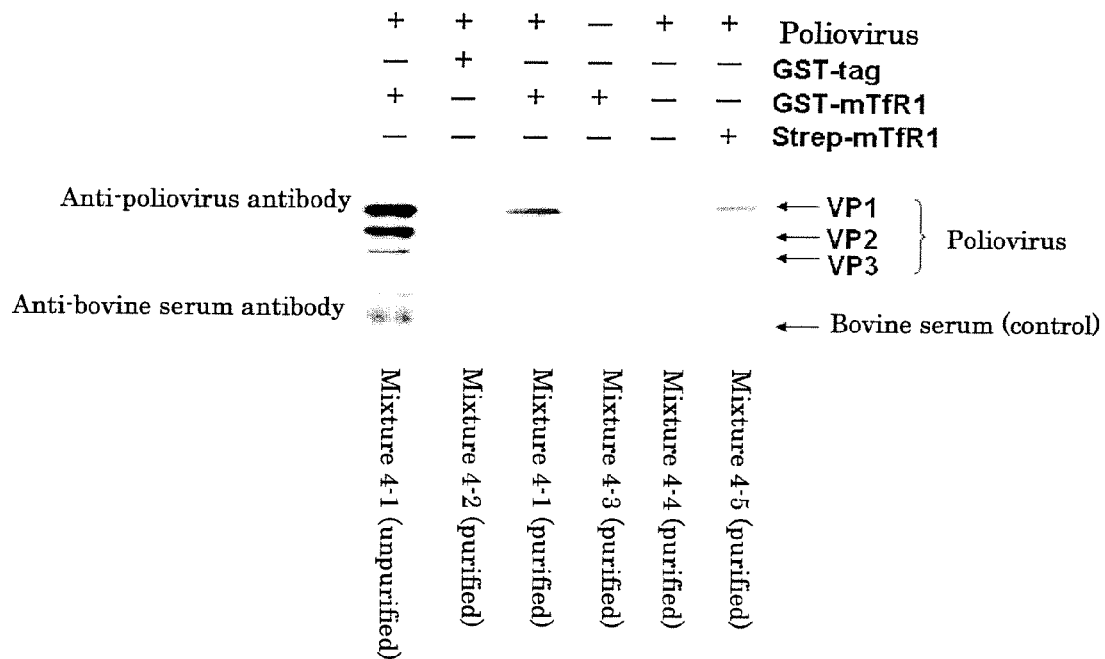
Figures 2, 7:
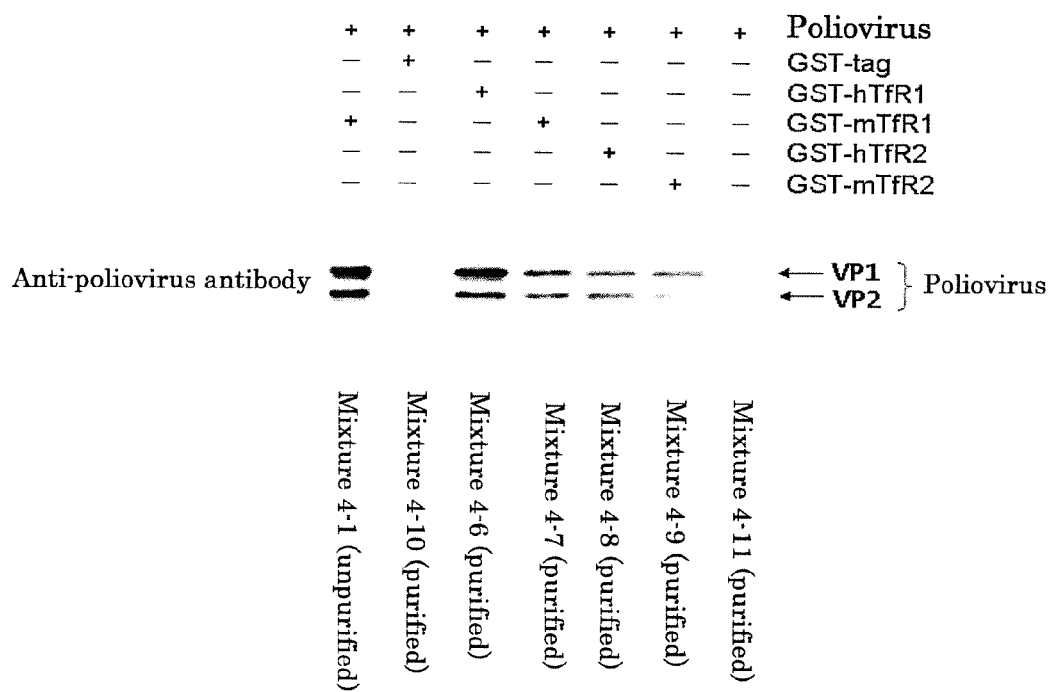

The results are presented in FIG. 7-1. In a positive control using the mixture containing poliovirus and Strep-mTfR1, a band was detected after purification. Also in the case of the mixture containing poliovirus and GST-mTfR1, a band was similarly detected after purification.

This result indicates that the amino acid sequence expressed by SEQ ID NO: 5 is directly involved with the binding to poliovirus.

Test Example 4-2

Identification of Binding Site of Poliovirus in the Transferrin Receptor

Binding capabilities between poliovirus and other transferrin receptors than mouse transferrin receptor 1 (mTfR1) were studied in the same manner as in Test Example 4-1.

—Preparation of GST-hTfR1—

The amino acid sequence expressed by the following SEQ ID NO: 6 is a partial sequence of human transferrin receptor 1 (hTfR1). The amino acid sequence expressed by the SEQ ID NO: 6 was cloned in a GST-tag expression vector (trade name: pGEX-p4X, product of Promega Co., Ltd.). The resultant product was used in the same manner as in Test Example 3 to prepare a GST-fused recombinant protein (hereinafter may be referred to as "GST-hTfR1").

(SEQ ID NO: 6)
318-TQFPPSRSS-326

—Preparation of GST-hTfR2—

The amino acid sequence expressed by the following SEQ ID NO: 7 is a partial sequence of human transferrin receptor 2 (hTfR2). The amino acid sequence expressed by the SEQ ID NO: 7 was cloned in a GST-tag expression vector (trade name: pGEX-p4X, product of Promega Co., Ltd.). The resultant product was used in the same manner as in Test Example 3 to prepare a GST-fused recombinant protein (hereinafter may be referred to as "GST-hTfR2").

(SEQ ID NO: 7)
341-TQFPPVASS-349

—Preparation of GST-mTfR2—

The amino acid sequence expressed by the following SEQ ID NO: 8 is a partial sequence of mouse transferrin receptor 2 (mTfR2). The amino acid sequence expressed by the SEQ ID NO: 8 was cloned in a GST-tag expression vector (trade name: pGEX-p4X, product of Promega Co., Ltd.). The resultant product was used in the same manner as in Test Example 3 to prepare a GST-fused recombinant protein (hereinafter may be referred to as "GST-mTfR2").

(SEQ ID NO: 8)
336-TQFPPVESS-344

—Preparation of Mixture 4-6—

The live poliovirus (100 μL) prepared in Test Example 2, the GST-hTfR1 (5 μg) and the STD buffer were mixed together so that the total amount of the mixture was 0.2 mL. The resultant mixture was incubated at 37° C. for 2 hours and then at 4° C. for 16 hours.

—Preparation of Mixture 4-7—

Mixture 4-7 was prepared in the same manner as in the preparation of the mixture 4-6 except that the GST-hTfR1 was changed to the GST-mTfR1 prepared in Test Example 4-1.

—Preparation of Mixture 4-8—

Mixture 4-8 was prepared in the same manner as in the preparation of the mixture 4-6 except that the GST-hTfR1 was changed to GST-hTfR2.

—Preparation of Mixture 4-9—

Mixture 4-9 was prepared in the same manner as in the preparation of the mixture 4-6 except that the GST-hTfR1 was changed to GST-mTfR2.

—Preparation of Mixture 4-10—

Mixture 4-10 was prepared in the same manner as in the preparation of the mixture 4-6 except that the GST-hTfR1 was changed to GST-tag (product of Promega Co., Ltd.).

—Preparation of Mixture 4-11—

Mixture 4-11 was prepared in the same manner as in the preparation of the mixture 4-6 except that the GST-hTfR1 was not added.

<Binding Test Between Transferrin Receptor and Poliovirus>

Using Glutathione-Sepharose (fast-flow) (product of GE Healthcare, Co., Ltd.), each of the mixtures 4-6 to 4-11 was subjected to the binding test between transferrin receptor and poliovirus in the same manner as in Test Example 4-1.

The supernatants of the purified mixtures 4-6 to 4-11 and the unpurified mixture 4-1 in Test Example 4-1 were treated in the same manner as in Test Example 2 to prepare samples for SDS-PAGE, which were subjected to SDS-PAGE and western blotting in the same manner as in Test Example 2.

The results are presented in FIG. 7-2. Similar to the results of the partial sequence (SEQ ID NO: 5) of mouse transferrin receptor 1 (mTfR1), it was found that the partial sequence (SEQ ID NO: 6) of human transferrin receptor 1 (hTfR1), the partial sequence (SEQ ID NO: 7) of human transferrin receptor 2 (hTfR2) and the partial sequence (SEQ ID NO: 8) of mouse transferrin receptor 2 (mTfR2) are directly involved with the binding to poliovirus.

Test Example 5

Identification of Binding Site of Poliovirus in the Transferrin Receptor

FIG. 8 depicts a stearic configuration (2.2 angstroms) of poliovirus (Mahoney strain) determined by X-ray crystallographic analysis (PDB ID:1HXS). The diameter of the virus particle was 30 nm. Black portions in the surface of poliovirus are dented portions in the poliovirus particle, and are called canyon. In the canyon, proteins called VP1, VP2 and VP3 exist. The binding capability of the VP1 to the transferrin receptor was studied by the following method.

—Preparation of MBP-VP1 GH Strand I—

Primers were designed based on the genome RNA sequence of poliovirus of the GeneBank registration number EF374015.1. With these primers, PCR was performed routinely using a cDNA sequence of poliovirus as a template to amplify a domain called a GH strand (the 637$^{th}$ base to the 735$^{th}$ base) in VP1 of poliovirus.

The gene fragment of the amplified VP1 GH strand I was cloned in an MBP expression vector (trade name: pMAL-p4X, product of New England Biolabs (NEB)). The resultant product was used for transformation in the same manner as in Test Example 3, to thereby prepare a fused recombinant protein of VP1 GH strand I and MBP (hereinafter may be referred to as "MBP-VP1 GH strand I").

Note that, the MBP-VP1 GH strand I has an amino acid sequence of the 213$^{th}$ residue to the 245$^{th}$ residue, represented by the following SEQ ID NO: 19, of a GH strand in VP1 of poliovirus.

```
                                        (SEQ ID NO: 19)
213-SKVPLKDQSAELGDSLYGAASLNDFGILAVRVV-245
```

—Preparation of MBP-VP1 GH Strand II—

Primers were designed based on the genome RNA sequence of poliovirus of the GeneBank registration number V01149. With these primers, PCR was performed routinely using a cDNA sequence of poliovirus as a template to amplify a domain called a GH strand (the 637$^{th}$ base to the 739$^{th}$ base) in VP1 of poliovirus.

A fused recombinant protein of VP1 GH strand II and MBP (hereinafter may be referred to as "MBP-VP1 GH strand II") was prepared in the same manner as in the preparation of MBP-VP1 GH strand I except that the gene fragment of VP1 GH strand I was changed to the gene fragment of VP1 GH strand II.

The MBP-VP1 GH strand II has an amino acid sequence of the 213$^{th}$ residue to the 245$^{th}$ residue, represented by the following SEQ ID NO: 20, of a GH strand in VP1 of poliovirus.

```
                                        (SEQ ID NO: 20)
213-SKVPLKDQSAALGDSLYGAASLNDFGILAVRVV-245
```

—Preparation of MBP-VP1 GH Loop—

A fragment (the 667$^{th}$ base to the 1,006$^{th}$ base) encoding a domain called a GH loop in VP1 of poliovirus was routinely amplified by PCR using a sense primer expressed by the following SEQ ID NO: 9 and an antisense primer expressed by the following SEQ ID NO: 10 designed based on the genome RNA sequence of poliovirus of the GeneBank registration number V01149.

A fused recombinant protein of VP1 GH loop and MBP (hereinafter may be referred to as "MBP-VP1 GH loop") was prepared in the same manner as in the preparation of MBP-VP1 GH strand I except that the gene fragment of VP1 GH strand I was changed to the gene fragment of VP1 GH loop.

Note that, the MBP-VP1 GH loop has an amino acid sequence of the 223$^{rd}$ residue to the 235$^{th}$ residue, represented by the following SEQ ID NO: 1, of a GH loop in VP1 of poliovirus.

```
Sense primer:
                                         (SEQ ID NO: 9)
5'-GCTCTAGAGACCAATCAGCAGCGTTGGGCGATTCACTTTATGGTGC

TGCATCC-3'

Antisense primer:
                                        (SEQ ID NO: 10)
5'-CCCAAGCTTCTATTATTAGTTCAAGGATGCAGCACCATAAAGTGAA

TC-3'

(SEQ ID NO: 1)
223-ALGDSLYGAASLN-235
```

—Preparation of Mixture 5-1—

The MBP-VP1 GH loop (0.5 μg), the GST-mTfR1 (5 μg) and the STD buffer were mixed together so that the total amount of the mixture was 10 μL. The resultant mixture was incubated at 23° C. for 2 hours and then at 4° C. for 16 hours.

—Preparation of Mixture 5-2—

Mixture 5-2 was prepared in the same manner as in the preparation of the mixture 5-1 except that the MBP-VP1 GH loop was not added.

—Preparation of mixture 5-3—

Mixture 5-3 was prepared in the same manner as in the preparation of the mixture 5-1 except that the MBP-VP1 GH loop was changed to MBP (product of NEB Co., Ltd.).

—Preparation of Mixture 5-4—

Mixture 5-4 was prepared in the same manner as in the preparation of the mixture 5-1 except that the MBP-VP1 GH loop was changed to MBP-VP1 GH strand I.

—Preparation of Mixture 5-5—

Mixture 5-5 was prepared in the same manner as in the preparation of the mixture 5-1 except that the MBP-VP1 GH loop was changed to MBP-VP1 GH strand II.

<Binding Test Between Poliovirus and Transferrin Receptor>

Each of the mixtures 5-1 to 5-5 was added to an amylose resin (trade name: Amylose-resin, product of NEB o., Ltd.), followed by incubating at 4° C. for 1 hour. The resultant mixture was centrifuged at 900 rpm for 3 min and the supernatant was discarded. 200 μL of the STD buffer containing 1% by mass Triton X-100 was added to the precipitate, and the mixture was centrifuged at 900 rpm for 3 min to wash the precipitate. This washing treatment was performed 5 times in total for purification. As a result of this purification, some compounds binding to the amylose resin (compounds having and/or binding to MBP) remained in the precipitate, and some compounds not binding thereto were washed out.

After purification, 8 μL of 20 mM maltose suspended in the STD buffer containing 1% by mass Triton X-100 was added to the obtained precipitate, and the mixture was centrifuged at 900 rpm for 3 min to obtain the supernatant. This treatment releases the bond between the amylose resin and the compound binding to the amylose resin, allowing it to flow into the supernatant.

The supernatants of the purified mixtures 5-1 to 5-5 and the unpurified mixture 5-1 were treated in the same manner as in Test Example 2 to prepare samples for SDS-PAGE, which were subjected to SDS-PAGE and western blotting according to routine methods.

Note that, the western blotting was performed using, as a primary antibody, an anti-GST antibody (trade name: Anti-GST-tag, mouse monoclonal antibody, product of MBL Co., Ltd.) and, as a secondary antibody, an anti-mouse IG-HRP antibody (trade name: Anti-mouse Ig-HRP, product of Dako Co., Ltd.).

The results are presented in FIG. 9. In the case of the mixture 5-1 of MBP-VP1 GH loop and GST-mTfR1, a band was detected even after purification. In addition, a band was also detected in the purified mixture 5-4 containing MBP-VP1 GH strand I and GST-mTfR1 and the purified mixture 5-5 containing MBP-VP1 GH strand II and GST-mTfR1.

This result indicates that the bond between poliovirus and transferrin receptor is due to the bond between the amino acid sequence expressed by SEQ ID NO: 1 in VP1 of poliovirus and the amino acid sequence expressed by SEQ ID NO: 5 in AD of the transferrin receptor.

Test Example 6

Identification of Biding Site of Poliovirus in the Transferrin Receptor

Binding capability between transferrin receptor and different domains in VP1 from that in Test Example 5 was studied by the following method.

—Preparation of MBP-VP1BC Loop—

A fragment (the $268^{th}$ base to the $327^{th}$ base) encoding a domain called a BC loop in VP1 of poliovirus was routinely amplified by PCR using a sense primer expressed by the following SEQ ID NO: 11 and an antisense primer expressed by the following SEQ ID NO: 12 designed based on the genome RNA sequence of poliovirus of the GeneBank registration number V01149.

The gene fragment of the amplified VP1BC loop was cloned in an MBP expression vector (trade name: pMAL-p4X, product of NEB). The resultant product was used for transformation in the same manner as in Test Example 3, to thereby prepare a fused recombinant protein of VP1BC loop and MBP (hereinafter may be referred to as "MBP-VP1BC loop").

Note that the MBC-VP1BC loop has an amino acid sequence of the $90^{th}$ residue to the $109^{th}$ residue, represented by the following SEQ ID NO: 2, of a BC loop in VP1 of poliovirus.

Sense primer:
(SEQ ID NO: 11)
5'-GCTCTAGAATGACTGTGGACAACCCGGCTTCTACTACAAACAAAGA

CAAATTGTTTTCT-3'

Antisense primer:
(SEQ ID NO: 12)
5'-CCCAAGCTTCTATTATTACTTCCACACAGAAAACAATTTGTCTTTG

TTTGTAGT-3'

(SEQ ID NO: 2)
91-MTVDNPASTTNKDKLFSVWK-109

—Preparation of MBP-VP1EF Loop—

A fragment (the $484^{th}$ base to the $507^{th}$ base) encoding a domain called an EF loop in VP1 of poliovirus was routinely amplified by PCR using a sense primer expressed by the following SEQ ID NO: 13 and an antisense primer expressed by the following SEQ ID NO: 14 designed based on the genome RNA sequence of poliovirus of the GeneBank registration number V01149.

A fused recombinant protein of VP1BC loop and MBP (hereinafter may be referred to as "MBP-VP1BC loop") was prepared in the same manner as in the preparation of MBP-VP1BC loop except that the gene fragment of VP1BC loop was changed to the gene fragment of VP1EF loop.

Note that, the MBP-VP1EF loop has an amino acid sequence of the $162^{th}$ residue to the $169^{th}$ residue, represented by the following SEQ ID NO: 3, of an EF loop in VP1 of poliovirus.

Sense primer:
(SEQ ID NO: 13)
5'-GCTCTAGACCAGGGGCACCGGTGCCAGAGAAATAAT-3'

Antisense primer:
(SEQ ID NO: 14)
5'-CCCAAGCTTCTATTATTATTTCTCTGGCACCGGTGC-3'

(SEQ ID NO: 3)
162-PGAVPEK-169

—Preparation of MBP-VP1EG Loop—

A fragment (the $528^{th}$ base to the $617^{th}$ base) encoding a domain called an FG loop in VP1 of poliovirus was routinely amplified by PCR using a sense primer expressed by the following SEQ ID NO: 21 and an antisense primer expressed by the following SEQ ID NO: 22 designed based on the genome RNA sequence of poliovirus of the GeneBank registration number V01149.

A fused recombinant protein of VP1FG loop and MBP (hereinafter may be referred to as "MBP-VP1FG loop") was prepared in the same manner as in the preparation of MBP-VP1BC loop except that the gene fragment of VP1BC loop was changed to the gene fragment of VP1EG loop.

Note that, the MBP-VP1EG loop has an amino acid sequence of the $176^{th}$ residue to the $205^{th}$ residue, represented by the following SEQ ID NO: 23, of an EG loop in VP1 of poliovirus.

Sense primer:
(SEQ ID NO: 21)
5'-GCTCTAGACAAACGTCCTCCAACCCATCAATTTTCTACACCTACGG

CACGGCACCAGCTCGAATT-3'

Antisense primer:
(SEQ ID NO: 22)
5'-CCCAAGCTTTTACTATTAATACGCGTTAGAAATGCCAACGTATGGA

ACCGAAATTCGAGCTGGTGCCGTGCCGTAGGT-3'

(SEQ ID NO: 23)
176-PSIFYTYGTAPARISVPYVGISNAY-205

—Preparation of MBP-VP1C Terminus—

A sense primer expressed by the following SEQ ID NO: 15 and an antisense primer expressed by the following SEQ ID NO: 16 were designed based on the genome RNA sequence of poliovirus of the GeneBank registration number V01149. With these primers, PCR was performed routinely using a cDNA sequence of poliovirus as a template to amplify a C terminal region (the $883^{th}$ base to the $906^{th}$ base) in VP1 of poliovirus.

A fused recombinant protein of VP1C terminal region and MBP (hereinafter may be referred to as "MBP-VP1C terminal region") was prepared in the same manner as in the preparation of MBP-VP1BC loop except that the gene fragment of VP1BC loop was changed to the gene fragment of the VP1C terminal region.

Note that, the MBP-VP1C terminal region has an amino acid sequence of the $295^{th}$ residue to the $302^{th}$ residue, represented by the following SEQ ID NO: 4, of a C terminal region in VP1 of poliovirus.

```
Sense primer:
                                    (SEQ ID NO: 15)
5'-GCTCTAGACTCGCTCCCTTATCCACCAAAGACCTGACAACGTACGC
TAG-3'

Antisense primer:
                                    (SEQ ID NO: 16)
5'-CCCAAGCTTCTATTATTAGTACGTTGTCAGGTCTTTGGTGGAT-3'

(SEQ ID NO: 4)
295-STKDLTTY-302
```

—Preparation of Mixture 6-1—

The MBP-VP1FG loop (0.5 μg), the GST-mTfR1 (5 μg) prepared in Test Example 4-1 and the STD buffer were mixed together so that the total amount of the mixture was 10 μL. The resultant mixture was incubated at 23° C. for 2 hours and then at 4° C. for 16 hours.

—Preparation of Mixture 6-2—

Mixture 6-2 was prepared in the same manner as in the preparation of the mixture 6-1 except that the MBP-VP1FG loop was changed to MBP.

—Preparation of Mixture 6-3—

Mixture 6-3 was prepared in the same manner as in the preparation of the mixture 6-1 except that the MBP-VP1FG loop was changed to MBP-VP1BC loop.

—Preparation of Mixture 6-4—

Mixture 6-4 was prepared in the same manner as in the preparation of the mixture 6-1 except that the MBP-VP1FG loop was changed to MBP-VP1EF loop.

—Preparation of Mixture 6-5—

Mixture 6-5 was prepared in the same manner as in the preparation of the mixture 6-1 except that the MBP-VP1FG loop was changed to MBP-VP1 GH loop prepared in Test Example 5.

—Preparation of Mixture 6-6—

Mixture 6-6 was prepared in the same manner as in the preparation of the mixture 6-1 except that the MBP-VP1FG loop was changed to MBP-VP1C terminus.

<Binding Test Between Poliovirus and Transferrin Receptor>

A binding test was performed in the same manner as in the binding test between poliovirus and transferrin receptor in Test Example 5 except that the mixtures 5-1 to 5-5 were changed to the mixtures 6-1 to 6-6.

The supernatants of the purified mixtures 6-1 to 6-6 and the unpurified mixture 6-1 were treated in the same manner as in Test Example 2 to prepare samples for SDS-PAGE, which were subjected to SDS-PAGE and western blotting in the same manner as in Test Example 5.

The results are presented in FIG. 10. A band was detected in all the mixtures except for the mixture 6-2 in which only MBP had been mixed with GST-mTfR1.

The results clearly indicates that the bond between poliovirus and transferrin receptor is due to the bond between the amino acid sequences expressed by SEQ ID NOs: 2 to 4 in VP1 of poliovirus and the amino acid sequence expressed by SEQ ID NO: 5 in AD of the transferrin receptor.

Test Example 7

Permeation of the Peptide Expressed by SEQ ID NO: 1 Through the Blood-Brain Barrier —Preparation of Alexa488-MBP-VP1 GH Loop—

Using Alexa Fluor (registered trademark) 488-Protein Labeling Kit (product of Invitrogen Co., Ltd.), Alexa Fluor (registered trademark) 488 was introduced to the primary amino acid moiety of the amino acid side chain of the MBP tag of the MBP-VP1 GH loop prepared in Test Example 5. Hereinafter, the fluorescence-labeled MBP-VP1 GH loop may be referred to as "Alexa488-MBP-VP1 GH loop."

The Alexa488-MBP-VP1 GH loop was prepared in the STD buffer so as to have a concentration of 2 mg/mL.

—Preparation of Alexa488-MBP—

MBP was fluorescence-labeled in the same manner as in the preparation of the Alexa488-MBP-VP1 GH loop except that the MBP-VP1 GH loop was changed to MBP2. Hereinafter, the fluorescence-labeled MBP may be referred to as "Alexa488-MBP."

The Alexa488-MBP was prepared using Alexa Fluor (registered trademark) 488-Protein Labeling Kit (product of Invitrogen Co., Ltd.) so as to have a concentration of 2 mg/mL.

<Permeation Test of the Peptide Expressed by SEQ ID NO: 1 Through the Blood-Brain Barrier>

A test was performed using the same in vitro model culture system of the blood-brain barrier as used in Test Example 1.

The Alexa488-MBP-VP1 GH loop (90 μg/mL), the fluorescence-labeled transferrin (Alexa Fluor (registered trademark) 488-transferrin (product of Invitrogen Co., Ltd.), hereinafter may be referred to as "Alexa488-Tf") (180 μg/mL), the Alexa488-MBP (90 μg/mL) or fluorescence-labeled dextran (Alexa Flor (registered trademark) 488-labelled dextran having a weight average molecular weight of 70 kDa, product of Invitrogen Co., Ltd.) (180 μg/mL) were added to the upper layer portion of the Transwell culture plate (product of Corning Incorporated). At 10 min, 20 min and 30 min after that, the culture in the lower layer portion of the Transwell culture plate was recovered and measured for fluorescence intensity with a spectrofluoro-photometer (trade name: F-2500, product of Hitachi High-Technologies Corporation). The fluorescence intensity was indicated as a permeation amount of poliovirus through the brain capillary endothelial cells in the Transwell.

The results are presented in FIG. 11. The PS value of the Alexa488-MBP-VP1 GH loop was 0.82, the PS value of the fluorescence-labeled transferrin was 0.33, the PS value of the Alexa488-MBP was 0.28, and the PS value of the fluorescence-labeled dextran was 0.33.

Similar to transferrin, the Alexa488-MBP-VP1 GH loop permeated the brain capillary endothelial cells, and also the permeation rate was almost the same.

This result indicates that the peptide containing the amino acid sequence expressed by SEQ ID NO: 1 could permeate the blood-brain barrier.

<Confirmation of Permeation Through the Blood-Brain Barrier by Observation with Confocal Microscope>

In the same manner as in Test Example 2, a full-length gene of transferrin receptor 1 (mTfR1) was prepared from a mouse cDNA by PCR using a sense primer expressed by the following SEQ ID NO: 24 and an antisense primer expressed by the following SEQ ID NO: 25 which were designed based on information of the GeneBank registration number BC054522.1.

```
Sense primer:
                                        (SEQ ID NO: 24)
5'-CCGCTCGAGGCCACCATGATGGATCAAGCCAGATCA-3'

Antisense primer:
                                        (SEQ ID NO: 25)
5'-CGCGGATCCCGAAACTCATTGTCAATATTCC-3'
```

The amplified gene fragment was inserted into an XhoI-BamHI cutting site of a red fluorescent protein expression vector (trade name: pmCherry-N1, product of Clontech Co., Ltd.) to thereby obtain an expression vector where mCherry was fused with the carboxyl terminus of mTfR1 (hereinafter may be referred to as "pmCherry-mTfR1"). The brain capillary endothelial cells used in Test Example 1 were transfected with the obtained expression vector using FuGENE6 (product of NEB Co., Ltd.) to express mCherry-mTfR1.

The Alexa488-MBP-VP1 GH loop was added to the brain capillary endothelial cells expressing the mCherry-mTfR1, and observed with a confocal microscope (product of Carl Zeiss Co., Ltd.) for 60 min.

As a result, it was observed that the transferrin receptor and the Alexa488-MBP-VP1 GH loop were bound to each other and taken in the brain capillary endothelial cells for about 20 min. Meanwhile, the Alexa488-MBP was not taken therein.

Figure 12A:
Figure 12B:
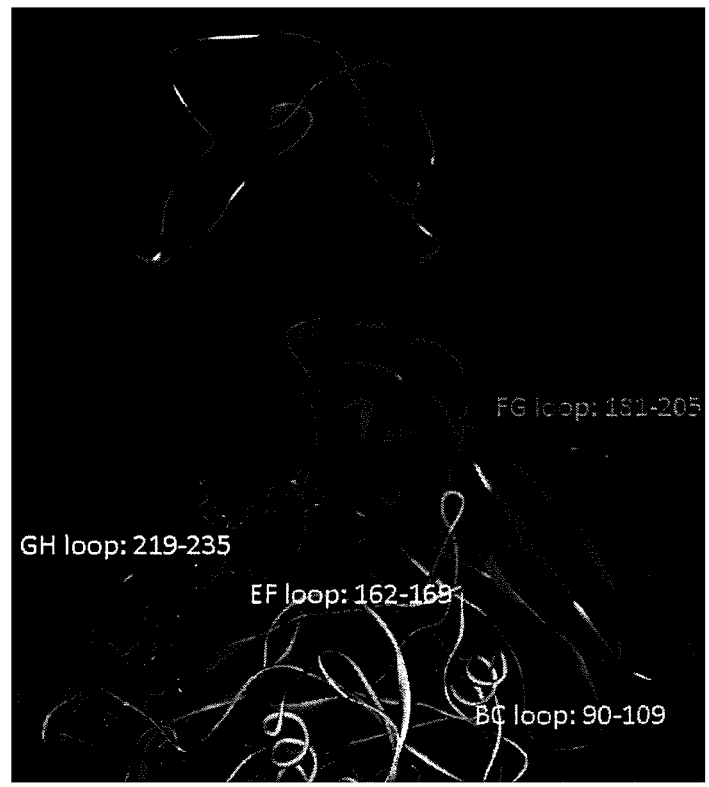
Figure 12C:
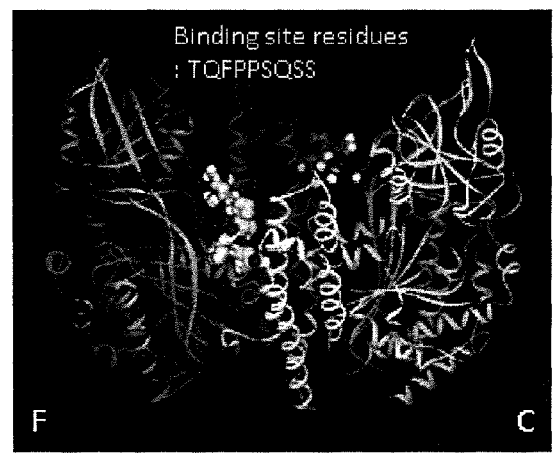
Figure 12D:
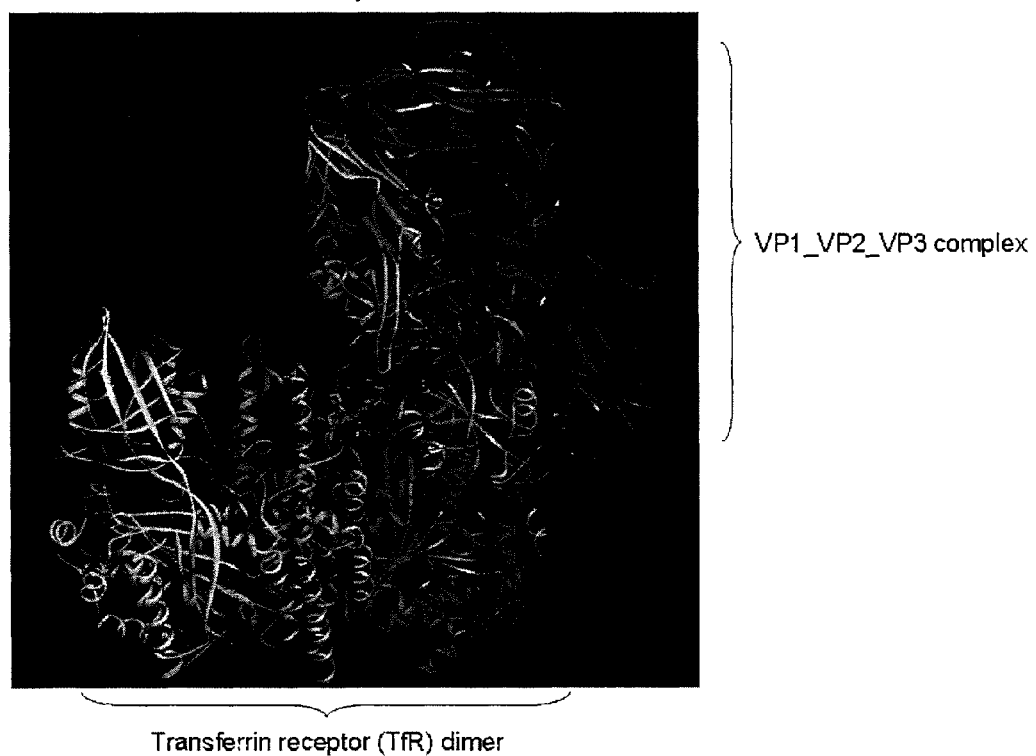

Based on the results obtained, docking simulation was performed on protein-protein interactions using E_RDock and ZDock. Analysis program used was a product of ACCELYS, Co., Ltd. FIG. 12A depicts a simulation model of a complex of VP1, VP2 and VP3 of poliovirus. FIG. 12B depicts a simulation model enlarging VP1. FIG. 12C depicts a simulation model of a transferrin receptor. FIG. 12D depicts a simulation model where the complex of FIG. 12A is bound to the transferrin receptor of FIG. 12C. The obtained calculation values confirmed that the amino acid sequence of the poliovirus expressed by SEQ ID NO: 1 binds to the amino acid sequence of the transferrin receptor expressed by SEQ ID NO: 5.

INDUSTRIAL APPLICABILITY

Since the peptide of the present invention can permeate the blood-brain barrier, it can suitably be used for, for example, a drug transporter capable of transporting a drug to a cell, especially a cell of the central nervous system, an antipoliovirus agent, a blood-brain barrier permeating agent and a transferrin receptor capturing body.

What is claimed is:

1. A peptide consisting of SEQ ID NO: 2.

2. The peptide according to claim 1, wherein the peptide binds to an amino acid sequence comprising SEQ ID NO: 5, SEQ ID NO: 6, SEQ ID NO: 7, SEQ ID NO: 8, or any combination thereof:

TQFPPSQSS;  (SEQ ID NO: 5)

TQFPPSRSS;  (SEQ ID NO: 6)

TQFPPVASS;  (SEQ ID NO: 7)
and

TQFPPVESS.  (SEQ ID NO: 8)

3. A drug transporter comprising:
a peptide consisting of SEQ ID NO: 2 and a carrier, wherein the carrier is a macromolecule, a microassembly, a microparticle, a microsphere, a nanosphere, a liposome or any combination thereof.

4. The drug transporter according to claim 3, further comprising: a drug carried in the carrier, wherein the drug is for diagnosis, prevention, treatment, or any combination thereof.

5. A blood-brain barrier permeating agent, comprising:
a peptide consisting of SEQ ID NO: 2 and a carrier, wherein the carrier is a macromolecule, a microassembly, a microparticle, a microsphere, a nanosphere, a liposome, or any combination thereof, and
wherein the blood-brain barrier permeating agent permeates blood-brain barrier.

6. A transferrin receptor capturing body, comprising:
a peptide consisting of SEQ ID NO: 2 and a carrier, wherein the carrier is a macromolecule, a microassembly, a microparticle, a microsphere, a nanosphere, a liposome, or any combination thereof, and
wherein the transferrin receptor capturing body binds to a transferrin receptor.

7. A drug transporter comprising:
a peptide consisting of SEQ ID NO: 1 and a carrier, wherein the carrier is a microassembly, a microparticle, a microsphere, a nanosphere, a liposome, an emulsion, or any combination thereof.

8. The drug transporter according to claim 7, further comprising: a drug carried in the carrier, wherein the drug is for diagnosis, prevention, treatment, or any combination thereof.

9. A blood-brain barrier permeating agent, comprising:
a peptide consisting of SEQ ID NO: 1 and a carrier, wherein the carrier is a microassembly, a microparticle, a microsphere, a nanosphere, a liposome, an emulsion, or any combination thereof, and
wherein the blood-brain barrier permeating agent permeates blood-brain barrier.

10. A transferrin receptor capturing body, comprising:
a peptide consisting of SEQ ID NO: 1 and a carrier, wherein the carrier is a macromolecule, a microassembly, a microparticle, a microsphere, a nanosphere, a liposome, an emulsion, or any combination thereof, and
wherein the transferrin receptor capturing body binds to a transferrin receptor.

11. A drug transporter comprising:
a peptide consisting of SEQ ID NO: 3 and a carrier, and
wherein the carrier is a microassembly, a microparticle, a microsphere, a nanosphere, a liposome, or any combination thereof.

12. The drug transporter according to claim 11, further comprising a drug carried in the carrier, wherein the drug is for diagnosis, prevention, treatment, or any combination thereof.

13. A blood-brain barrier permeating agent, comprising:
a peptide consisting of SEQ ID NO: 3 and a carrier, wherein the carrier is a microassembly, a microparticle, a microsphere, a nanosphere, a liposome, or any combination thereof, and
wherein the blood-brain barrier permeating agent permeates blood-brain barrier.

14. A transferrin receptor capturing body, comprising:
a peptide consisting of SEQ ID NO: 3 and a carrier, wherein the carrier is a macromolecule, a microassembly, a microparticle, a microsphere, a nanosphere, a liposome, or any combination thereof and,
wherein the transferrin receptor capturing body binds to a transferrin receptor.

15. A drug transporter comprising:
a peptide consisting of SEQ ID NO: 4 and a carrier, wherein the carrier is a microassembly, a microparticle, a microsphere, a nanosphere, a liposome, an emulsion, or any combination thereof.

16. The drug transporter according to claim 15, further comprising: a drug carried in the carrier, wherein the drug is for diagnosis, prevention, treatment, or any combination thereof.

17. A blood-brain barrier permeating agent, comprising:
a peptide consisting of SEQ ID NO: 4 and a carrier,
wherein the carrier is a microassembly, a microparticle, a microsphere, a nanosphere, a liposome, an emulsion, or any combination thereof, and
wherein the blood-brain barrier permeating agent permeates blood-brain barrier.

18. A transferrin receptor capturing body, comprising:
a peptide consisting of SEQ ID NO: 4 and a carrier,
wherein the carrier is a microassembly, a microparticle, a microsphere, a nanosphere, a liposome, an emulsion, or any combination thereof, and
wherein the transferrin receptor capturing body binds to a transferrin receptor.

* * * * *